(12) United States Patent
Vakoc et al.

(10) Patent No.: US 11,852,474 B2
(45) Date of Patent: Dec. 26, 2023

(54) ACTIVE QUADRATURE DEMODULATION FOR SUBSAMPLED/CIRCULAR RANGING OPTICAL COHERENCE TOMOGRAPHY

(71) Applicant: The General Hospital Corporation, Boston, MA (US)

(72) Inventors: Benjamin J. Vakoc, Arlington, MA (US); Norman Lippok, Quincy, MA (US)

(73) Assignee: The General Hospital Corporation, Boston, MA (US)

( * ) Notice: Subject to any disclaimer, the term of this patent is extended or adjusted under 35 U.S.C. 154(b) by 252 days.

(21) Appl. No.: 17/264,165

(22) PCT Filed: Jul. 30, 2019

(86) PCT No.: PCT/US2019/044111
§ 371 (c)(1),
(2) Date: Jan. 28, 2021

(87) PCT Pub. No.: WO2020/028346
PCT Pub. Date: Feb. 6, 2020

(65) Prior Publication Data
US 2021/0318111 A1    Oct. 14, 2021

Related U.S. Application Data

(60) Provisional application No. 62/799,582, filed on Jan. 31, 2019, provisional application No. 62/711,728, filed on Jul. 30, 2018.

(51) Int. Cl.
*G01B 9/02* (2022.01)
*G01B 9/02001* (2022.01)
(Continued)

(52) U.S. Cl.
CPC ....... *G01B 9/0201* (2013.01); *G01B 9/02008* (2013.01); *G01B 9/02091* (2013.01);
(Continued)

(58) Field of Classification Search
CPC .............. G01B 9/0201; G01B 9/02008; G01B 9/02091; G01B 9/02005; G01B 9/02079;
(Continued)

(56) References Cited

U.S. PATENT DOCUMENTS 5,390,023 A    2/1995  Biegen
5,442,719 A *  8/1995  Chang .................. G02B 6/1345
                                              385/132
(Continued)

FOREIGN PATENT DOCUMENTS

JP    2006201087 A    8/2006
WO    2017139760 A1   8/2017

OTHER PUBLICATIONS

An, L. et al, "Use of a scanner to modulate spatial interferograms for in vivo full-range Fourier domain optical coherence tomography," Optics Letters 32(23), 3423-3425 (2007).
(Continued)

*Primary Examiner* — Hwa Andrew Lee
(74) *Attorney, Agent, or Firm* — QUARLES & BRADY LLP

(57) ABSTRACT

A method including: scanning a sample over a period of time using an electro-magnetic radiation source, the period of time including a first time period and a second time period, a sample portion of the electro-magnetic radiation source being directed to the sample in a sample arm of an optical interferometric system, and a reference portion of the electro-magnetic radiation source being directed to a reference arm of the optical interferometric system; applying, using a phase modulator, a phase shift comprising a first phase shift
(Continued)

and a second phase shift to at least one of the reference portion or the sample portion of the electro-magnetic radiation source, the first phase shift being applied during the first time period and the second phase shift being applied during the second time period, the second phase shift having a difference of 90 degrees from the first phase shift; acquiring in-phase data based on a first interference between first backscattered electro-magnetic radiation during the first time period and the at least one of the reference portion or the sample portion subjected to the first phase shift; acquiring quadrature data based on a second interference between second backscattered electro-magnetic radiation during the second time period and the at least one of the reference portion or the sample portion subjected to the second phase shift; and determining a complex interference signal based on the in-phase data and the quadrature data.

38 Claims, 23 Drawing Sheets

(51) Int. Cl.
    *G01B 9/02091*     (2022.01)
    *G06T 7/00*     (2017.01)
(52) U.S. Cl.
    CPC .. *G06T 7/0012* (2013.01); *G06T 2207/10101* (2013.01); *G06T 2207/30004* (2013.01)
(58) Field of Classification Search
    CPC ......... G06T 7/0012; G06T 2207/10101; G06T 2207/30004; A61B 5/0066; G01J 3/28
    See application file for complete search history.

(56) References Cited

U.S. PATENT DOCUMENTS

| | | | |
|---|---|---|---|
| 7,236,250 B2 | 6/2007 | Iwai | |
| 7,733,497 B2 | 6/2010 | Yun | |
| 2009/0002713 A1* | 1/2009 | Ohbayashi | ......... G01B 9/02091 356/477 |

OTHER PUBLICATIONS

Baumann, B. et al, "Full range complex spectral domain optical coherence tomography without additional phase shifters," Optics Express 15(20), 13375-13387 (2007).
Choma, M.A. et al, "Instantaneous quadrature low-coherence interferometry with 3x3 fiber-optic couplers," Optics Letters 28(22) 2162-2164 (2003).
Davis, A.M. et al, "Heterodyne swept-source optical coherence tomography for complete complex conjugate ambiguity removal," Journal of Biomedical Optics 10(6), 064005 (2005).
Götzinger, E., et al. "High speed full range complex spectral domain optical coherence tomography." Optics express 13.2 (2005): 583-594.
Hofer, B. et al, "Dispersion encoded full range frequency domain optical coherence tomography," Optics Express 17(1), 7-24 (2009).
Huber, R. et al, "Fourier Domain Mode Locking (FDML): A new laser operating regime and applications for optical coherence tomography," Opt. Express 14, 3225-3237 (2006).
International Searching Authority. International Search Report and Written Opinion for application PCT/US2019/044111, dated Oct. 25, 2019. 10 pages.
Jayaraman, V. et al, "Rapidly swept, ultra widely-tunable 1060 nm MEMS-VCSELs," Electron. Lett. 48, 1331-1333 (2012).
Ji, X. et al, "Chip-based frequency combs sources for optical coherence tomography," arXiv: 1902.07695 (2019).

Jun, C. et al, "All-fiber wavelength swept ring laser based on Fabry-Perot filter for optical frequency domain imaging," Opt. Express 22, 25805-25814 (2014).
Khazaeinezhad, R., et al. "16 MHz wavelength-swept and wavelength-stepped laser architectures based on stretched-pulse active mode locking with a single continuously chirped fiber Bragg grating." Optics letters 42.10 (2017): 2046-2049.
Leitgeb, R.A. et al, "Complex ambiguity-free Fourier domain optical coherence tomography through transverse scanning," Optics Letters 32(23), 3453-3455 (2007).
Leitgeb, R.A. et al, "Phase-shifting algorithm to achieve high-speed long-depth-range probing by frequency-domain optical coherence tomography," Optics Letters 28, 2201-2203 (2003).
Lippok, N. et al, "Extended coherence length and depth ranging using a Fourier-domain mode-locked frequency comb and circular interferometric ranging," Physical Review Applied 11, 014018 (2019).
Marchand, P.J. et al, "Soliton microcomb based spectral domain optical coherence tomography," arXiv: 1902.06985 (2019).
Murata, S. et al, "Tuning ranges for 1.5 _m wavelength tunable DBR lasers," Electron. Lett. 24, 577-579 (1988).
Oh, W.-Y. et al, ">400 kHz repetition rate wavelength-swept laser and application to high-speed optical frequency domain imaging," Opt. Lett. 35, 2919-2921 (2010).
Pfeiffer, T. et al, "Ultra low noise Fourier domain mode locked laser for high quality megahertz optical coherence tomography," Biomed. Opt. Express 9, 4130-4148 (2018).
Sarunic, M.V. et al, "Instantaneous complex conjugate resolved spectral domain and swept-source OCT using 3x3 fiber couplers," Optics Express 13(3), 957-967 (2005).
Sarunic, M.V. et al, "Real-time quadrature projection complex conjugate resolved Fourier domain optical coherence tomography," Optics Letters 31(16), 2426-2428 (2006).
Siddiqui, M. et al, "Optical-domain subsampling for data efficient depth ranging in Fourier-domain optical coherence tomography," Optics Express 20(16), 17938-17951 (2012).
Siddiqui, M., et al. "Compensation of spectral and RF errors in swept-source OCT for high extinction complex demodulation." Optics express 23.5 (2015): 5508-5520.
Siddiqui, M., et al. "High-speed optical coherence tomography by circular interferometric ranging." Nature photonics 12.2 (2018): 111-116.
Tao, Y.K. et al, "High-speed complex conjugate resolved retinal spectral domain optical coherence tomography using sinusoidal phase modulation," Optics Letters 32(20), 2918-2920 (2007).
Tozburun, S. et al, "A rapid, dispersion-based wavelength-stepped and wavelength-swept laser for optical coherence tomography," Opt. Express 22, 3414-3424 (2014).
Tsai, T.-H. et al, "Frequency comb swept lasers," Opt. Express 17, 21257-21270 (2009).
Vakhtin, A.B. et al, "Resolving the complex conjugate ambiguity in Fourier-domain OCT by harmonic lock-in detection of the spectral interferogram," Optics Letters 31(9), 1271-1273 (2006).
Vakoc, B.J. et al, "Elimination of depth degeneracy in optical frequencydomain imaging through polarization-based optical demodulation," Optics Letters 31(3), 362-364 (2006).
Wang, H. et al, "Extending the effective imaging range of Fourier-domain optical coherence tomography using a fiber optic switch," Optics Letters 33(22), 2632-2634 (2008).
Wang, Z. et al, "Cubic meter volume optical coherence tomography," Optica 3, 1496-1503 (2016).
Wieser, W. et al, "Multi-Megahertz OCT: High quality 3D imaging at 20 million A-scans and 4.5 GVoxels per second," Opt. Express 18, 14685-14704 (2010).
Wojtkowski, M. et al, "Full range complex spectral optical coherence tomography technique in eye imaging," Optics Letters 27(16), 1415-1417 (2002).
Yasuno, Y. et al, "Simultaneous B-M-mode scanning method for real-time full-range Fourier domain optical coherence tomography," Applied Optics 45(8), 1861-1865 (2006).
Yun, S-H, et al. "Removing the depth-degeneracy in optical frequency domain imaging with frequency shifting." Optics express 12.20 (2004): 4822-4828.

(56) References Cited

OTHER PUBLICATIONS

Zhang, J. et al, "Removal of a mirror image and enhancement of the signal-to-noise ratio in Fourier-domain optical coherence tomography using an electrooptic phase modulator," Optics Letters 30(2), 147-149 (2005).
Zvyagin, A.V. et al, "Achromatic optical phase shifter-modulator," Optics Letters 26(4), 187-189 (2001).
Fabritius et al., Complex Conjugate Resolved Retinal Imaging by One-micrometer Spectral Domain Optical Coherence Tomography Using an Electro-optical Phase Modulator, Journal of the Optical Society of Korea, 2011, 15(2):111-117.
Lippok et al., High Speed Demodulation in Circular Ranging Optical Coherence Tomography Using a LiNbO3 Phase Modulator and a Stretched Pulse Active Mode-Locked Frequency Comb Laser at 1.3 um, Proc. of SPIE-OSA, 2019, vol. 11078, pp. 1107804-1 thru 1107804-3.
Vergnole et al., Artifact Removal in Fourier-Domain Optical Coherence Tomography with a Piezoelectric Fiber Stretcher, Optics Letters, 2008, 33(7):732-734.
European Patent Office, Extended Search Report, Application No. 19845420.9, dated Mar. 29, 2022, 9 pages.
Japan Patent Office, Notification of Reasons for Refusal, Application No. 2021-505427, dated Feb. 28, 2023, 19 pages.
Japan Patent Office, Decision to Grant a Patent, Application No. 2021-505427, dated Jun. 7, 2023, 6 pages.

\* cited by examiner

US 11,852,474 B2

ACTIVE QUADRATURE DEMODULATION FOR SUBSAMPLED/CIRCULAR RANGING OPTICAL COHERENCE TOMOGRAPHY

CROSS-REFERENCE TO RELATED APPLICATIONS

This application is a U.S. National Stage of International Application No. PCT/US2019/044111 filed Jul. 30, 2019 which is based on, claims the benefit of, and claims priority to U.S. Provisional Application No. 62/711,728, filed Jul. 30, 2018, and U.S. Provisional Application No. 62/799,582, filed, Jan. 31, 2019, each of which is hereby incorporated herein by reference in its entirety for all purposes.

STATEMENT REGARDING FEDERALLY SPONSORED RESEARCH

This invention was made with government support under P41EB015903 awarded by the National Institutes of Health (NIH). The government has certain rights in the invention.

BACKGROUND

The acquisition in the frequency domain has enhanced the sensitivity and imaging speed of optical coherence tomography techniques by orders of magnitude but imposes constraints on the acquisition bandwidth that either limit imaging range, optical bandwidth, or both. Coherent circular ranging (CR) allows imaging at high speed and with long range and high axial resolution, simultaneously. By using optical frequency combs, the depth space of the interferometric signal is folded, enabling long imaging ranges at much reduced RF bandwidths. CR combines the high imaging speed and sensitivity of Fourier domain techniques with the long imaging range known from time domain OCT. Unfortunately, the use of frequency combs generates RF errors that cause artifacts when imaging at multiples of the principal measurement range of the frequency comb free spectral range (FSR). To access the full depth range, it is beneficial to implement efficient, high-speed, and stable methods to acquire analytic (otherwise known as complex) interference signals. In certain prior reports of CR, this has been achieved by passive polarization-based optical quadrature demodulation. Although this method has reduced artifacts by more than 50 dB, it uses a relatively complex optical circuit and best performance has been obtained when paired with frequent recalibration routines. A more robust method to perform demodulation could simplify the construction and operation of these CR systems.

SUMMARY OF THE PRESENT DISCLOSURE

Accordingly, in various embodiments the present invention discloses active phase modulation methods which use a phase modulator (PM) to provide stable I/Q demodulation of detected signals such that a complex signal including both real in-phase (I) and imaginary quadrature (Q) signal components at high laser repetition speeds up to and beyond 1 MHz can be obtained, making it feasible to use CR for clinical and industrial applications.

In one embodiment of the invention, a method is provided which includes: scanning a sample over a period of time using an electro-magnetic radiation source, the period of time including a first time period and a second time period, a sample portion of the electro-magnetic radiation source being directed to the sample in a sample arm of an optical interferometric system, and a reference portion of the electro-magnetic radiation source being directed to a reference arm of the optical interferometric system; applying, using a phase modulator, a phase shift including a first phase shift and a second phase shift to at least one of the reference portion or the sample portion of the electro-magnetic radiation source, the first phase shift being applied during the first time period and the second phase shift being applied during the second time period, the second phase shift having a difference of 90 degrees from the first phase shift; acquiring in-phase data based on a first interference between first backscattered electro-magnetic radiation during the first time period and the at least one of the reference portion or the sample portion subjected to the first phase shift; acquiring quadrature data based on a second interference between second backscattered electro-magnetic radiation during the second time period and the at least one of the reference portion or the sample portion subjected to the second phase shift; and determining a complex interference signal based on the in-phase data and the quadrature data.

In some embodiments, the first phase shift is 0 degrees during the first time period and the second phase shift is 90 degrees during the second time period.

In some embodiments, applying a phase shift further includes: applying the phase shift to the reference portion of the electro-magnetic radiation source, acquiring in-phase data further includes: acquiring the in-phase data based on the first interference between the first backscattered electro-magnetic radiation during the first time period and the reference portion subjected to the first phase shift, acquiring quadrature data further includes: acquiring the quadrature data based on the second interference between the second backscattered electro-magnetic radiation during the second time period and the reference portion subjected to the second phase shift, and determining a complex interference signal further includes: determining the complex interference signal based on the in-phase data and the quadrature data.

In some embodiments, the electro-magnetic radiation source emits a plurality of electro-magnetic radiation pulses, the plurality of electro-magnetic radiation pulses includes a first A-line including a first subset of the plurality of electro-magnetic radiation pulses emitted during the first time period and a second A-line including a second subset of the plurality of electro-magnetic radiation pulses emitted during the second time period, and scanning the sample further includes: scanning the sample using the first A-line during the first time period and the second A-line during the second time period.

In some embodiments, the first subset of the plurality of electro-magnetic radiation pulses corresponds to a particular sequence of wavenumbers, and the second subset of the plurality of electro-magnetic radiation pulses corresponds to the particular sequence of wavenumbers.

In some embodiments, a first wavenumber of the particular sequence of wavenumbers is different from a second wavenumber of the particular sequence of wavenumbers.

In some embodiments, the first A-line is scanned at a first location in the sample and the second A-line is scanned at a second location in the sample different from the first location.

In some embodiments, the electro-magnetic radiation source emits a third A-line including a third subset of the plurality of electro-magnetic radiation pulses emitted during a third time period and corresponding to the particular sequence of wavenumbers, scanning the sample further includes: scanning the sample using the third A-line during the third time period; applying the phase shift further includes: applying a 0 degree phase shift to the reference portion of the electro-magnetic radiation source during the third time period; the in-phase data includes first in-phase data, the quadrature data includes second quadrature data, acquiring in-phase data further includes: acquiring third in-phase data based on a third interference between third backscattered electro-magnetic radiation during the third time period and the 0-degree shifted reference portion; and determining the complex interference signal further includes: determining second in-phase data based on interpolating between the first in-phase data and the third in-phase data, and determining the complex interference signal based on the second in-phase data and the second quadrature data.

In some embodiments, the electro-magnetic radiation source emits a beam having a beam diameter, wherein a distance between the first location and the second location is one quarter of the beam diameter or less.

In some embodiments, the electro-magnetic radiation source emits a plurality of electro-magnetic radiation pulses, and each of the plurality of electro-magnetic radiation pulses is divided into two time periods corresponding to the first time period and the second time period.

In some embodiments, the method further includes: providing a modified electro-magnetic radiation source based on combining the plurality of electro-magnetic radiation pulses with a delayed copy of the plurality of electro-magnetic radiation pulses; and scanning the sample further includes: scanning the sample using the modified electro-magnetic radiation source, wherein the modified electro-magnetic radiation source emits the plurality of electro-magnetic pulses each occurring during the first time period alternating with the respective plurality of delayed pulses each occurring during the second time period.

In some embodiments, providing a modified electro-magnetic radiation source includes: providing the modified electro-magnetic radiation source based on combining the plurality of electro-magnetic radiation pulses with the delayed copy of the plurality of electro-magnetic radiation pulses, wherein the delayed copy of the plurality of electro-magnetic radiation pulses is delayed by a time less than a time of one of the plurality of the electro-magnetic radiation pulses.

In some embodiments, determining the complex interference signal further includes: determining the complex interference signal based on applying a depth dependent calibration to correct for additional phase shift from a detection system.

In some embodiments, acquiring in-phase data further includes: acquiring an in-phase frame associated with the first phase shift; acquiring quadrature data further includes: acquiring a quadrature frame associated with the second phase shift; and the method further includes: generating a phase difference frame based on a difference of phases between the in-phase frame and the quadrature frame, determining a correction factor based on the phase difference frame, applying the correction factor to the in-phase frame and the quadrature frame, and determining a complex interference frame based on the corrected in-phase frame and the corrected quadrature frame.

In some embodiments, determining a correction factor further includes: determining a mean phase difference based on the phase difference frame, and determining the correction factor based on a difference between the mean phase difference and a 90 degree phase shift.

In some embodiments, determining the mean phase difference further includes: determining a histogram of phase differences in the phase difference frame, and identifying the mean phase difference based on the histogram of phase differences.

In some embodiments, the electro-magnetic radiation source includes an optically subsampled wavelength stepped source (OSWSS).

In some embodiments, the electro-magnetic radiation source includes a chirped fiber Bragg grating stretched-pulse mode-locked (CFBG-SPML) laser.

In some embodiments, the CFBG-SPML laser includes a 1.3 μm imaging band.

In some embodiments, the phase modulator includes a lithium niobate phase modulator.

In another embodiment of the invention, an apparatus is provided which includes: an optical interferometric system including a sample arm and a reference arm; at least one phase modulator associated with at least one of the reference arm or the sample arm of the optical interferometric system; an electro-magnetic radiation source coupled to the optical interferometric system, the electro-magnetic radiation source scanning a sample over a period of time, the period of time including a first time period and a second time period, a sample portion of the electro-magnetic radiation source being directed to the sample in the sample arm of the optical interferometric system, a reference portion of the electro-magnetic radiation source being directed to the reference arm of the optical interferometric system, and a phase shift including a first phase shift and a second phase shift being applied to at least one of the reference portion or the sample portion of the electro-magnetic radiation source by the at least one phase modulator, the first phase shift being applied during the first time period and the second phase shift being applied during the second time period, the second phase shift having a difference of 90 degrees from the first phase shift; and a microprocessor coupled to the phase modulator and the electro-magnetic radiation source, the microprocessor to: acquire in-phase data based on a first interference between first backscattered electro-magnetic radiation during the first time period and the at least one of the reference portion or the sample portion subjected to the first phase shift, acquire quadrature data based on a second interference between second backscattered electro-magnetic radiation during the second time period and the at least one of the reference portion or the sample portion subjected to the second phase shift, and determine a complex interference signal based on the in-phase data and the quadrature data.

In some embodiments, the first phase shift is 0 degrees during the first time period and the second phase shift is 90 degrees during the second time period.

In some embodiments, the phase shift is applied to the reference portion of the electro-magnetic radiation source by the at least one phase modulator, the microprocessor, when acquiring in-phase data, is further to: acquire the in-phase data based on the first interference between the first backscattered electro-magnetic radiation during the first time period and the reference portion subjected to the first phase shift, the microprocessor, when acquiring quadrature data, is further to: acquire the quadrature data based on the second interference between the second backscattered electro-magnetic radiation during the second time period and the reference portion subjected to the second phase shift, and the microprocessor, when determining a complex interference signal, is further to: determine the complex interference signal based on the in-phase data and the quadrature data.

In some embodiments, the electro-magnetic radiation source emits a plurality of electro-magnetic radiation pulses, the plurality of electro-magnetic radiation pulses includes a first A-line including a first subset of the plurality of electro-magnetic radiation pulses emitted during the first time period and a second A-line including a second subset of the plurality of electro-magnetic radiation pulses emitted during the second time period, and the electro-magnetic radiation source is further to: scan the sample using the first A-line during the first time period and the second A-line during the second time period.

In some embodiments, the first subset of the plurality of electro-magnetic radiation pulses corresponds to a particular sequence of wavenumbers, and the second subset of the plurality of electro-magnetic radiation pulses corresponds to the particular sequence of wavenumbers.

In some embodiments, a first wavenumber of the particular sequence of wavenumbers is different from a second wavenumber of the particular sequence of wavenumbers.

In some embodiments, the first A-line is scanned at a first location in the sample and the second A-line is scanned at a second location in the sample different from the first location.

In some embodiments, the electro-magnetic radiation source emits a third A-line including a third subset of the plurality of electro-magnetic radiation pulses emitted during a third time period and corresponding to the particular sequence of wavenumbers, the electro-magnetic radiation source is further to: scan the sample using the third A-line during the third time period; the phase modulator is further to: apply a 0 degree phase shift to the reference portion of the electro-magnetic radiation source during the third time period; the in-phase data includes first in-phase data, the quadrature data includes second quadrature data, the microprocessor, when acquiring in-phase data, is further to: acquire third in-phase data based on a third interference between third backscattered electro-magnetic radiation during the third time period and the 0-degree shifted reference portion; and the microprocessor, when determining the complex interference signal, is further to: determine second in-phase data based on interpolating between the first in-phase data and the third in-phase data, and determine the complex interference signal based on the second in-phase data and the second quadrature data.

In some embodiments, the electro-magnetic radiation source emits a beam having a beam diameter, a distance between the first location and the second location is one quarter of the beam diameter or less.

In some embodiments, the electro-magnetic radiation source is further to: emit a plurality of electro-magnetic radiation pulses, wherein each of the plurality of electro-magnetic radiation pulses is divided into two time periods corresponding to the first time period and the second time period.

In some embodiments, the microprocessor is further to: provide a modified electro-magnetic radiation source based on combining the plurality of electro-magnetic radiation pulses with a delayed copy of the plurality of electro-magnetic radiation pulses; and the electro-magnetic radiation source is further to: scan the sample using the modified electro-magnetic radiation source, wherein the modified electro-magnetic radiation source emits the plurality of electro-magnetic pulses each occurring during the first time alternating with the respective plurality of delayed pulses each occurring during the second time.

In some embodiments, the microprocessor, when providing a modified electro-magnetic radiation source, is further to: provide the modified electro-magnetic radiation source based on combining the plurality of electro-magnetic radiation pulses with the delayed copy of the plurality of electro-magnetic radiation pulses, wherein the delayed copy of the plurality of electro-magnetic radiation pulses is delayed by a time less than a time of one of the plurality of the electro-magnetic radiation pulses.

In some embodiments, the microprocessor, when determining the complex interference signal, is further to: determine the complex interference signal based on applying a depth dependent calibration to correct for additional phase shift from a detection system.

In some embodiments, the microprocessor, when acquiring in-phase data, is further to: acquire an in-phase frame associated with the first phase shift; the microprocessor, when acquiring quadrature data, is further to: acquire a quadrature frame associated with the second phase shift; and the microprocessor is further to: generate a phase difference frame based on a difference of phases between the in-phase frame and the quadrature frame, determine a correction factor based on the phase difference frame, apply the correction factor to the in-phase frame and the quadrature frame, and determine a complex interference frame based on the corrected in-phase frame and the corrected quadrature frame.

In some embodiments, the microprocessor, when determining a correction factor, is further to: determine a mean phase difference based on the phase difference frame, and determine the correction factor based on a difference between the mean phase difference and a 90 degree phase shift.

In some embodiments, the microprocessor, when determining the mean phase difference, is further to: determine a histogram of phase differences in the phase difference frame, and identify the mean phase difference based on the histogram of phase differences.

In some embodiments, the electro-magnetic radiation source includes an optically subsampled wavelength stepped source (OSWSS).

In some embodiments, the electro-magnetic radiation source includes a chirped fiber Bragg grating stretched-pulse mode-locked (CFBG-SPML) laser.

In some embodiments, the CFBG-SPML laser includes a 1.3 μm imaging band.

In some embodiments, the at least one phase modulator includes a lithium niobate phase modulator.

In still another embodiment of the invention, a method is provided which includes: scanning a sample over a period of time using an electro-magnetic radiation source, the period of time including a first time period and a second time period, a sample portion of the electro-magnetic radiation source being directed to the sample in a sample arm of an optical interferometric system, and a reference portion of the electro-magnetic radiation source being directed to a reference arm of the optical interferometric system; applying, using a phase modulator, a phase shift including a first phase shift and a second phase shift to at least one of the reference portion or the sample portion of the electro-magnetic radiation source, the first phase shift being applied during the first time period and the second phase shift being applied during the second time period, the second phase shift having a difference of 90 degrees from the first phase shift; acquiring in-phase frame data based on a first interference between first backscattered electro-magnetic radiation during the first time period and the at least one of the reference portion or the sample portion subjected to the first phase shift; acquiring quadrature frame data based on a second interference between second backscattered electro-magnetic radiation during the second time period and the at least one of the reference portion or the sample portion subjected to the second phase shift; generating a phase difference frame based on a difference of phases between the in-phase frame data and the quadrature frame data; determining a correction factor based on the phase difference frame; applying the correction factor to the in-phase frame data and the quadrature frame data; and determining a complex interference frame based on the corrected in-phase frame and the corrected quadrature frame.

In some embodiments, determining a correction factor further includes: determining a mean phase difference based on the phase difference frame, and determining the correction factor based on a difference between the mean phase difference and a 90 degree phase shift.

In some embodiments, determining the mean phase difference further includes: determining a histogram of phase differences in the phase difference frame, and identifying the mean phase difference based on the histogram of phase differences.

In some embodiments, the electro-magnetic radiation source includes a chirped fiber Bragg grating stretched-pulse mode-locked (CFBG-SPML) laser.

In some embodiments, the CFBG-SPML laser includes a 1.3 μm imaging band.

In some embodiments, the phase modulator includes a lithium niobate phase modulator.

In yet another embodiment of the invention, an apparatus is provided which includes: an optical interferometric system including a sample arm and a reference arm; at least one phase modulator associated with at least one of the reference arm or the sample arm of the optical interferometric system; an electro-magnetic radiation source coupled to the optical interferometric system, the electro-magnetic radiation source scanning a sample over a period of time, the period of time including a first time period and a second time period, a sample portion of the electro-magnetic radiation source being directed to the sample in the sample arm of the optical interferometric system, a reference portion of the electro-magnetic radiation source being directed to the reference arm of the optical interferometric system, and a phase shift including a first phase shift and a second phase shift being applied to at least one of the reference portion or the sample portion of the electro-magnetic radiation source by the at least one phase modulator, the first phase shift being applied during the first time period and the second phase shift being applied during the second time period, the second phase shift having a difference of 90 degrees from the first phase shift; and a microprocessor coupled to the phase modulator and the electro-magnetic radiation source, the microprocessor to: acquire in-phase frame data based on a first interference between first backscattered electro-magnetic radiation during the first time period and the at least one of the reference portion or the sample portion subjected to the first phase shift, acquire quadrature frame data based on a second interference between second backscattered electro-magnetic radiation during the second time period and the at least one of the reference portion or the sample portion subjected to the second phase shift, generate a phase difference frame based on a difference of phases between the in-phase frame data and the quadrature frame data, determine a correction factor based on the phase difference frame, apply the correction factor to the in-phase frame data and the quadrature frame data, and determine a complex interference frame based on the corrected in-phase frame data and the corrected quadrature frame data.

In some embodiments, the microprocessor, when determining a correction factor, is further to: determine a mean phase difference based on the phase difference frame, and determine the correction factor based on a difference between the mean phase difference and a 90 degree phase shift.

In some embodiments, the microprocessor, when determining the mean phase difference, is further to: determine a histogram of phase differences in the phase difference frame, and identify the mean phase difference based on the histogram of phase differences.

In some embodiments, the electro-magnetic radiation source includes a chirped fiber Bragg grating stretched-pulse mode-locked (CFBG-SPML) laser.

In some embodiments, the CFBG-SPML laser includes a 1.3 μm imaging band.

In some embodiments, the at least one phase modulator includes a lithium niobate phase modulator.

The foregoing and other aspects and advantages of the present disclosure will appear from the following description. In the description, reference is made to the accompanying drawings that form a part hereof, and in which there is shown by way of illustration one or more exemplary versions. These versions do not necessarily represent the full scope of the invention.

BRIEF DESCRIPTION OF THE DRAWINGS

The following drawings are provided to help illustrate various features of example embodiments of the disclosure, and are not intended to limit the scope of the disclosure or exclude alternative implementations.

DETAILED DESCRIPTION OF THE PRESENT DISCLOSURE

Figure 1:
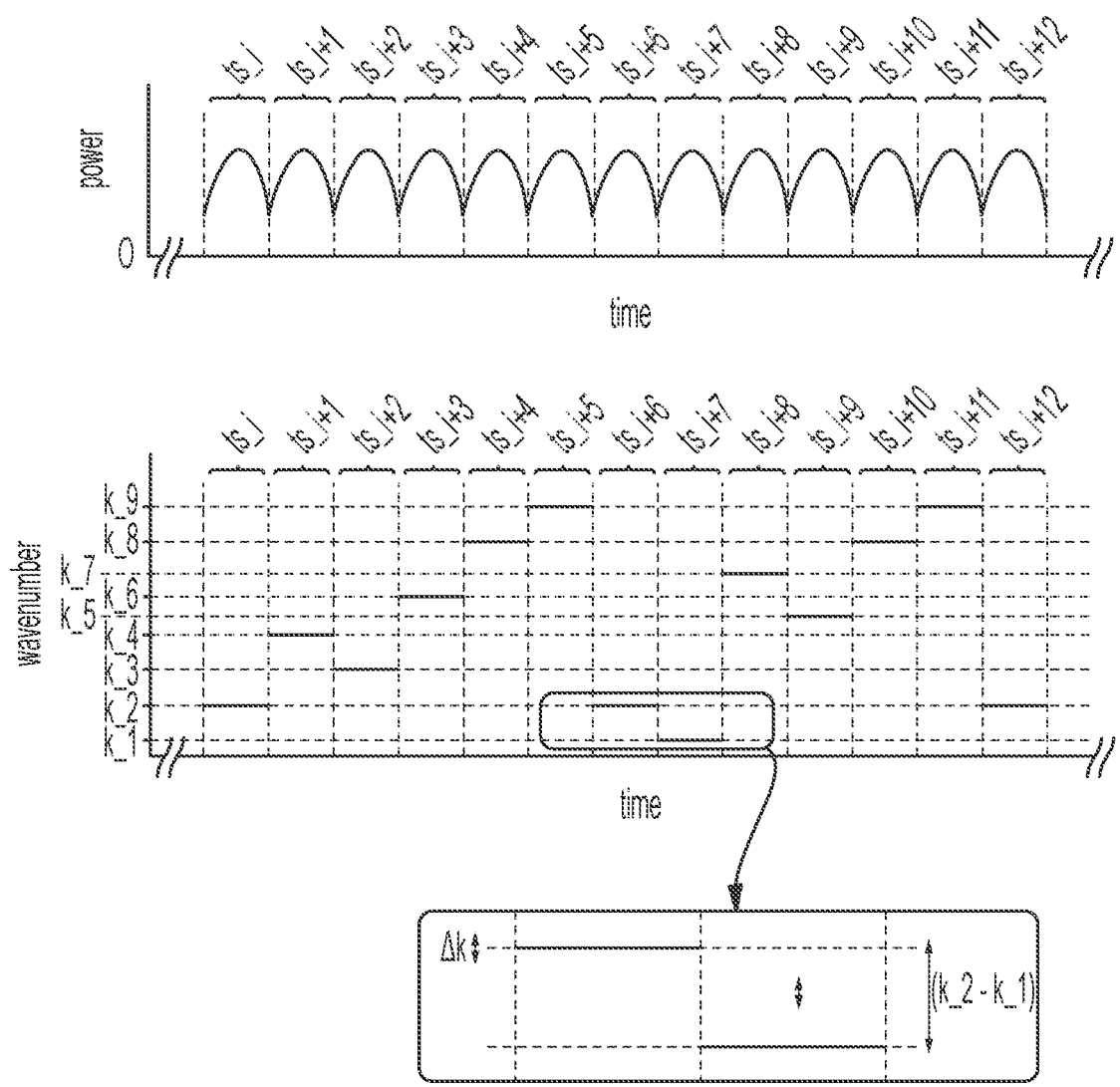
FIG. 1 shows an optically subsampled wavelength stepped source (OSWSS) (top), a schematic graph of power output of an OSWSS over time for a series of pulses ts_i to ts_i+12 (center), an arrangement of wavenumbers for the OSWSS for each of the series of pulses ts_i to ts_i+12 (bottom), and a close-up of two such wavenumbers k_2 and k_1 (bottom, inset).

Before any embodiments of the invention are explained in detail, it is to be understood that the invention is not limited in its application to the details of construction and the arrangement of components set forth in the following description or illustrated in the attached drawings. The invention is capable of other embodiments and of being practiced or of being carried out in various ways. Also, it is to be understood that the phraseology and terminology used herein is for the purpose of description and should not be regarded as limiting. For example, the use herein of "including," "comprising," or "having" and variations thereof is meant to encompass the items listed thereafter and equivalents thereof as well as additional items.

In various embodiments, the invention provides methods and apparatus for generating a complex interference signal and using the signal for demodulation of data obtained using subsampled/circular ranging optical coherence tomography. Various techniques are disclosed for obtaining quadrature electric field components (π/2/90 degree phase shifted relative to one another) by actively (electronically) controlling the phase of the interferometric signal to obtain the complex interferometric signal and mitigate imaging artefacts at very high imaging speeds (e.g. at MHz laser repetition rates).

In certain embodiments, a preferred implementation for phase modulation uses a Lithium Niobate ($LiNbO_3$) phase modulator device which converts a voltage signal to an optical phase shift, although other methods of phase modulating a light beam can be used. Other methods of inducing phase shifts in an optical beam can also be used including, but not limited to, other electro-optic phase modulators such as those based on silicon or semiconductor materials, thermal phase modulators that use temperature to affect optical beam phase, and acousto-optic phase modulators that translate acoustic waves or acoustic energy into optical phase shifts. An example architecture which incorporates a phase modulator is described below.

Thus, disclosed herein are techniques for using active phase shifting (e.g. phase modulation) in either or both of the sample and reference arms of an interferometric system to generate a complex interference signal associated with each time period (referred to herein as a "timeslot," see below) of an Optically Subsampled Wavelength-Stepped Source (OSWSS). The techniques may include: hardware embodiments that describe the placement and driving of phase-shifting arrangements in the interferometer; arrangements to synchronize the phase shifting signal to the OSWSS and/or the detector arrangements and/or the microscope; signal processing methods to generate the complex signal from the measured signals; and signal processing methods and arrangements to calibrate and compensate for demodulation errors from various sources.

The techniques may be performed in an "inter-pulse" manner or an "intra-pulse" manner. Inter-pulse techniques use at least two different pulses (which may or may not be at the same wavenumber; see below for discussion of wavenumber) to generate the complex interference signal associated with a single wavenumber. Intra-pulse techniques use measurements within a single pulse to generate the complex signal associated with the wavenumber of that pulse. Inter-pulse methods are more straightforward to implement but may require more additional pulses per complex measurement and may slow imaging speed as a result. Intra-pulse methods are more complex to implement, but may allow the fastest imaging by requiring only a single pulse to collect the data that is required for generating a complex signal (i.e. two signals that are 90 degrees phase shifted relative to one another).

Optically Subsampled Wavelength-Stepped Sources (OSWSS)

Disclosed herein are apparatus and methods for performing quadrature demodulation (also referred to as in-phase (I)/quadrature (Q) demodulation or I/Q demodulation) in the context of an interferometric measurement system that uses a particular source, namely an optically subsampled wavelength stepped source (OSWSS). The following is an overview of OSWSS sources that may be used in implementations of the I/Q demodulation embodiments disclosed herein.

An OSWSS, shown diagrammatically in FIG. 1 (top), provides a specific optical output signal having one or more of the following properties and parameters:

the OSWSS provides an optical output that steps discretely between optical wavelengths (also referred to as optical wavenumbers (i.e. the spatial frequency of a wave) or optical frequencies) in time;

the OSWSS output can be divided into a set of contiguous timeslots where is i refers to the ith timeslot (FIG. 1, center);

each timeslot ts_i has a particular duration. Timeslots often have the same duration, but do not necessarily need to and in various embodiments have different durations;

a timeslot is defined as a period of time in which the laser provides light with a specific optical wavenumber and the timeslot ends when the laser begins providing light with a different optical wavenumber. The laser wavenumber transitions discretely between wavenumbers during a transition across timeslots. This is illustrated in FIG. 1 (bottom) which shows an exemplary time/wavenumber relationship. Here, ts_i produces wavenumber k_2, and ts_i+1 produces wavenumber k_4, etc.;

the OSWSS output has a certain finite linewidth Δk as illustrated in FIG. 1 (bottom, inset). Here, this linewidth is less than the mean wavenumber difference between adjacent timeslots, indicating that the source provides distinct wavenumber outputs at each timeslot. This shows a clear distinction between this laser and a source with continuously swept wavenumber outputs; and the light within a timeslot is referred to as a pulse. It can have a varying power that rises and falls during each timeslot as shown in FIG. 1 (center), or it can have constant power. In both scenarios, the light within a timeslot is referred to herein as a pulse because it describes a finite duration of light at the associated wavenumber.

Examples of OSWSS sources include sources designed to produce wavenumbers that are equally spaced in wavenumber space, e.g., a frequency comb source.

Interferometric Measurements Using an OSWSS

Figure 2:
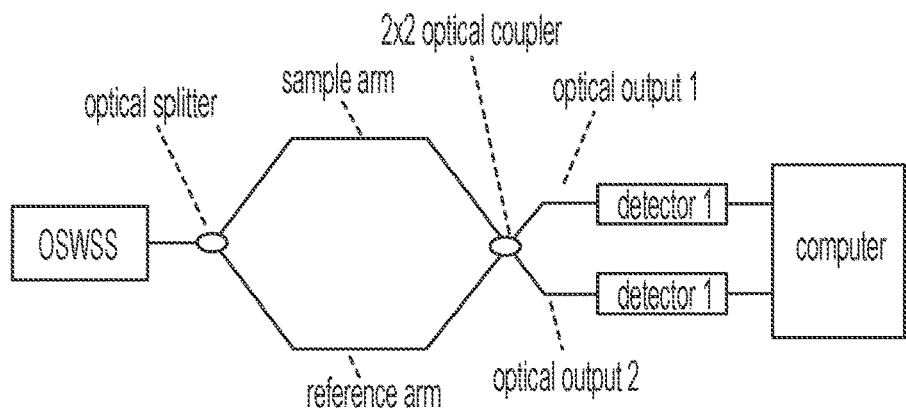
FIG. 2 shows an embodiment of an interferometric system which uses an OSWSS.

FIG. 2 shows a generalized setup for making interferometric measurements using an OSWSS. Components include a source such as the OSWSS; an interferometer including a sample arm and a reference arm; the interferometer outputs; the detectors; and the signal processing computer/arrangement which in various embodiments includes a processor/microprocessor. The use of an OSWSS with an interferometer allows ranging measurements such as those performed in optically subsampled optical coherence tomography, or more generally to interrogate an object in the sample arm using interferometric methods. I/Q demodulation is used to measure a complex output signal from the interferometer as described below.

In the absence of I/Q demodulation, a (non-complex) interference signal may be measured. This signal is proportional to the sine of the phase difference between the sample and reference arm light. On the other hand, using I/Q demodulation a complex interference signal may be measured which has a real component proportional to the sine of the aforementioned phase difference and an imaginary component proportional to the cosine of the aforementioned phase difference. Using I/Q demodulation, the complex interference signal resulting from a given positive optical delay (+d) in an interferometric ranging system is distinguishable from that given by a negative optical delay of the same magnitude (−d), a distinction that cannot be made when measuring non-complex interference signals. In subsampled OCT, this ability to discriminate between positive and negative delays allows circular ranging (CR) to reduce a large physical delay space to a reduced circular delay space.

In the simplest implementation of an interferometer such as that shown in FIG. 2 and in the absence of I/Q demodulation, both output signals 1 and 2 would be proportional to the sine of the phase difference between the sample and reference arm light. I/Q demodulation can be performed in such a system using methods such as redesigning the way sample and reference arm light are combined (for example, using polarization-based optical demodulation) or, as disclosed herein, by modulating the phase of the light in one or both of the sample and reference arm at different time points, so that at one time point the outputs are proportional to the sine of the phase difference and a later time point the outputs are proportional to the cosine of the phase difference. More generally, the measurements acquired over time can be combined, for example using a computer processor, to generate the complex fringe using additional signal processing.

In various embodiments, inter-pulse phase modulation includes modulating the phase of the light in the reference or sample arm between pulses (or, equivalently, between timeslots) so that, for example, data obtained from a set of two pulses can be used to generate a complex signal, with the first pulse giving rise to the sine component and the second pulse giving rise to the cosine component.

Figure 3:
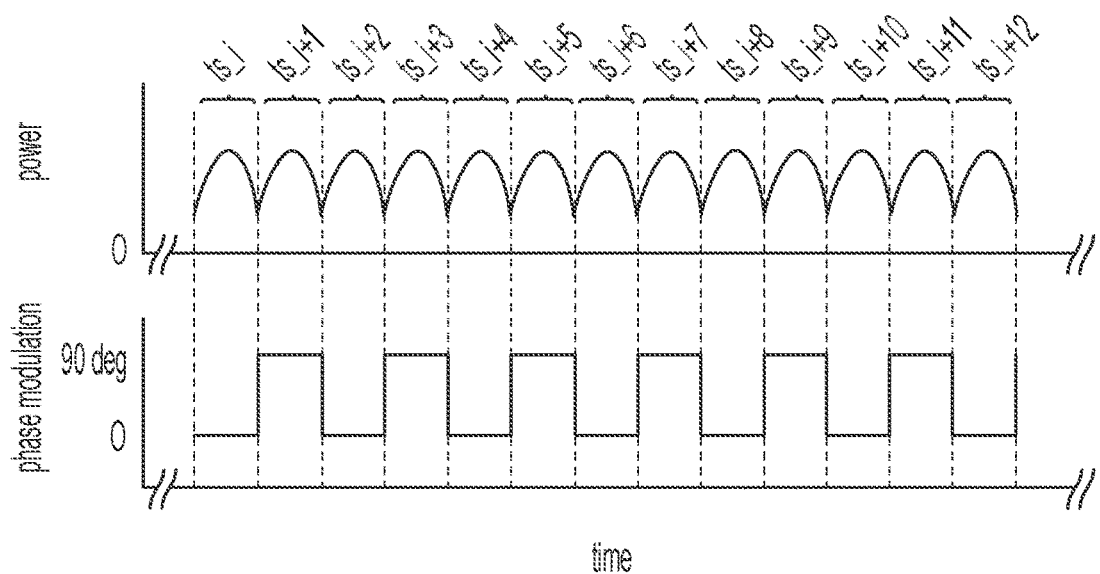
FIG. 3 shows power and phase modulation levels for an embodiment in which the phase is switched between 0 degrees for even-numbered timeslots to 90 degrees for odd-numbered timeslots (upper panel) or when phase is switched between 0 degrees and 90 degrees every sixth timeslot (lower panel).
Figure 3:
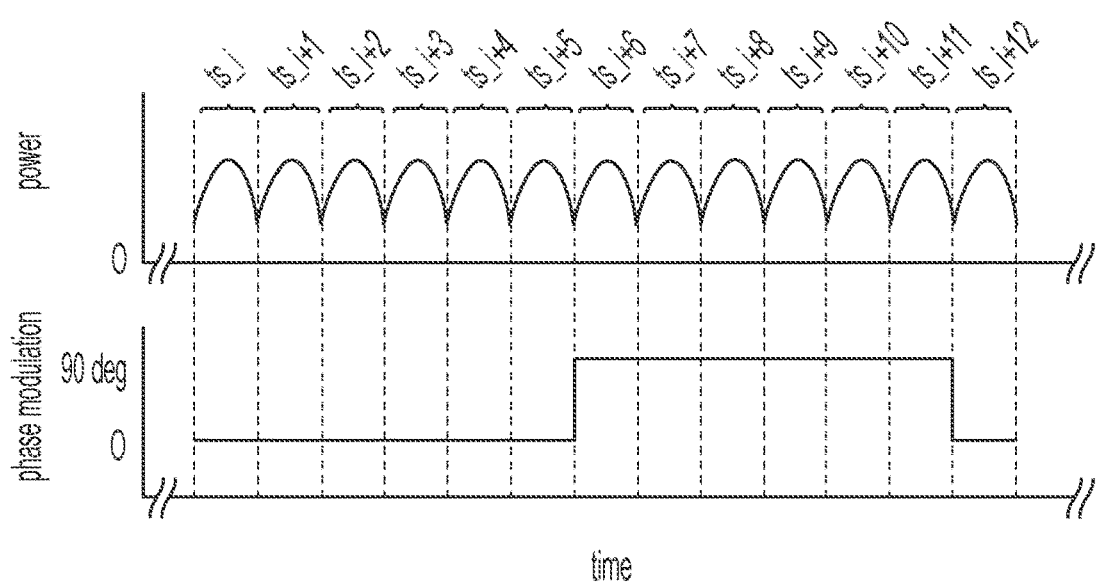

In the example shown in FIG. 3 (upper panel), a phase modulation is induced that is 0 degrees for even-numbered timeslots/pulses (e.g. ts_i, ts_i+2, etc.), and 90 degrees for odd-numbered timeslots/pulses (e.g. ts_i+1, ts_i+3, etc.). Although the phase is indicated to be varied between 0 and 90 degrees in many of the embodiments disclosed herein, in various embodiments the phase can be varied between other angles provided that there is a 90 degree ($\pi/2$) difference between the angles. In this example, assuming that timeslot/pulse ts_i and ts_i+3 have the same wavenumber k, then pulse ts_i can be used to measure the sine interference signal associated with wavenumber k, and pulse ts_i+3 can be used to measure the cosine (due to the 90 degree phase shift introduced into the data associated with pulse ts_i+3) interference signal associated with wavenumber k. In the example shown in the lower panel of FIG. 3, the phase modulation changes every six pulses. Here, assuming that timeslot/pulse ts_i and ts_i+6 have the same wavenumber k, then timeslot/pulse ts_i and ts_i+6 can be used to determine the sine and cosine interference signals, respectively, in order to generate the complex fringe signal associated with wavenumber k.

Phase Modulation Between Successive A-Lines

Figure 4A:
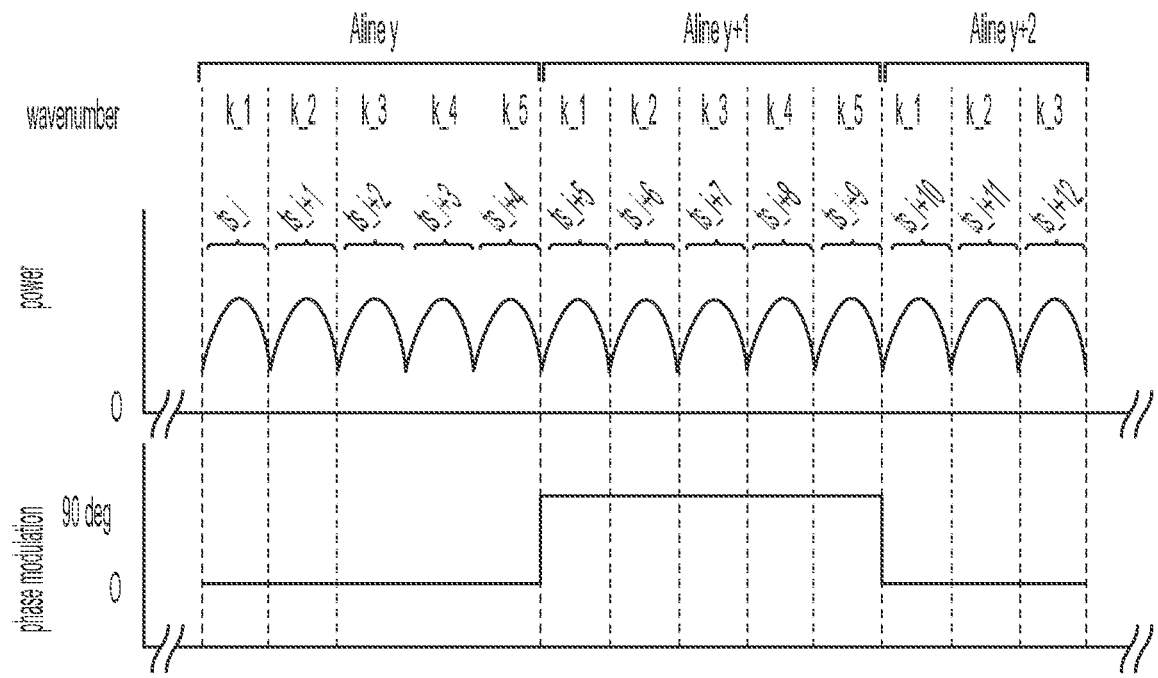
FIG. 4A shows wavenumbers, power, and phase modulation levels for an embodiment in which the wavenumbers k_1 to k_5 repeat every five timeslots and the phase alternates between 0 degrees and 90 degrees every five timeslots.

In some embodiments, phase modulation may be performed between successive A-lines. In one particular embodiment, an A-line includes a set of pulses with a specific wavenumber sequence and this wavenumber sequence is repeated for each subsequent A-line. This is illustrated in FIG. 4A which shows the output of an OSWSS having five wavenumbers numbered k_1 to k_5 which repeat, where each set of wavenumbers k_1 to k_5 denotes a single A-line. Thus A-line y and y+1 measure the same properties (using the same sequence of wavenumbers) but at different times. In this embodiment, adjacent/sequential A-lines are phase-shifted to have a 90 degree relationship as shown in FIG. 4A. The signals from A-line y are used to form the sine (real) fringe signal, and the signals from A-line y+1 are used to form the cosine (imaginary) fringe signal. Combined, A-lines y and y+1 form a single complex A-line that can be used to perform I/Q demodulation.

Figure 4B:
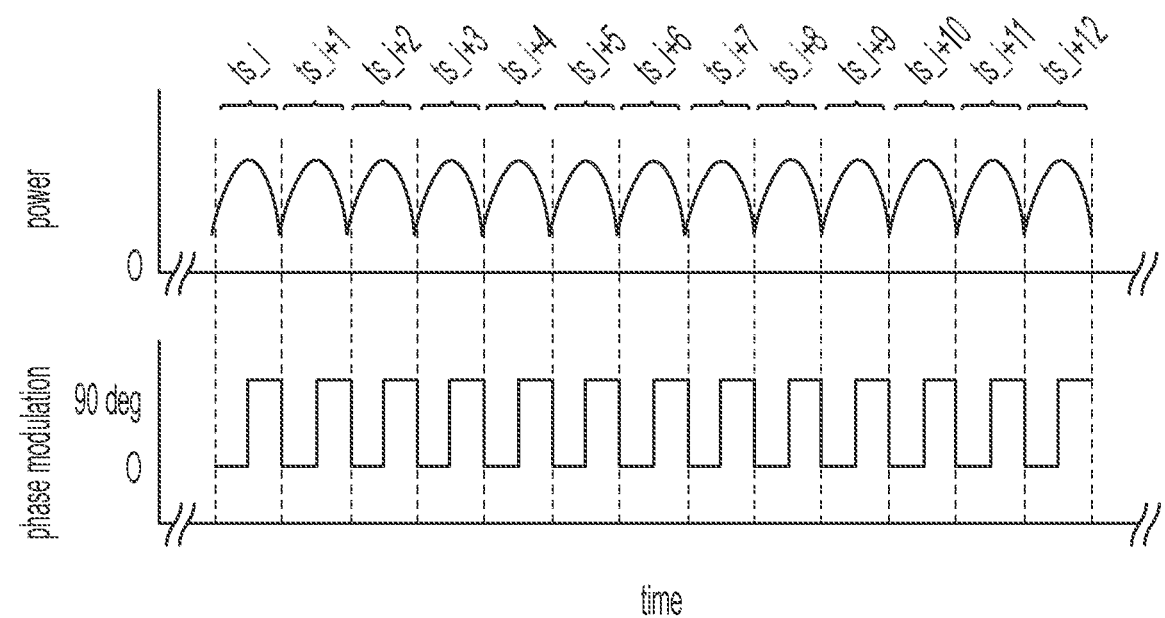
FIG. 4B shows power and phase modulation levels for an embodiment in which the phase is switched between 0 degrees and 90 degrees within a timeslot.

In some embodiments, phase modulation may be performed within a timeslot which includes embodiments wherein phase modulation occurs within a pulse. This is illustrated in FIG. 4B. Here, a single timeslot is divided into at least two smaller time-slots where a first phase signal is applied during the first, and a second phase signal is applied during the second. In FIG. 4B, a 90 degree phase shift is induced between these smaller time-slots. As such, both the in-phase and quadrature components can be measured for a single laser pulse/timeslot. Here, at least two measurements per timeslot are used.

Figure 5:
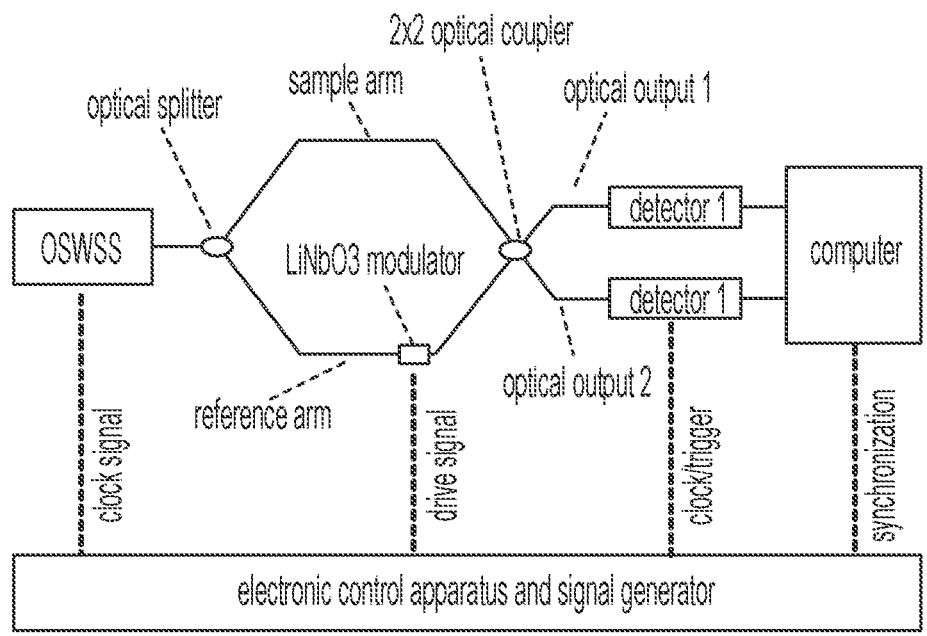
FIG. 5 shows an embodiment of an interferometric system which includes a phase modulator in the reference arm and which has a controller to coordinate the functions of one or more of the OSWSS, the phase modulator, the detector(s), and the computing system.

An example architecture which incorporates a phase modulator (e.g. a Lithium Niobate ($LiNbO_3$) phase modulator device) is shown in FIG. 5. FIG. 5 shows an embodiment of an interferometric system which includes a phase modulator in the reference arm and which has a controller (electronic control apparatus and signal generator, which may include a processor/microprocessor) to coordinate the functions of one or more of the OSWSS, the phase modulator, the detector(s), and the computing system.

In certain embodiments, a beam emitting a series of A-lines (each of which includes the same sequence of wavenumbers) may be applied to a sample to obtain data as the beam is scanned across the sample. In an OCT system such as this in which a beam is scanned across a sample, the two A-lines used to construct the complex fringe as described herein may be from scans of different portions of the sample, and thus in some instances it may be necessary to make corrections to the data to account for the sample differences between pairs of data points.

Figure 6:
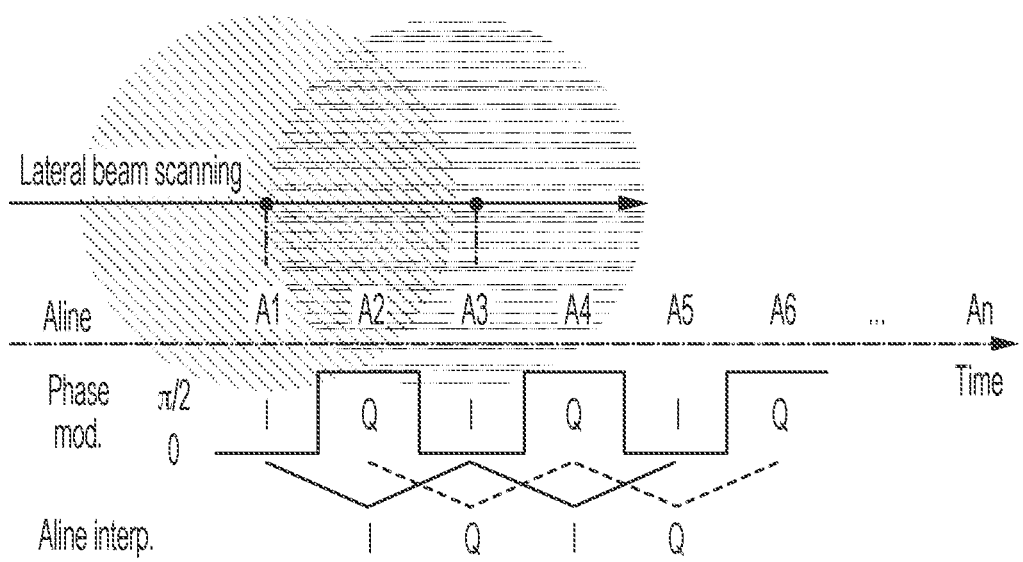
FIG. 6 shows the location of a scanning beam at two positions, corresponding to A-lines A1 and A3, along with indications of other A-line locations, phase modulation states, and possible interpolations that can be performed between A-lines.

This phenomenon is illustrated in FIG. 6 which shows the beam profiles (circular) for A-line A1 and A-line A3. Here, A-lines A1 and A3 provide in-phase (I or sine) fringes and A-line 2 provides quadrature (Q or cosine) fringes. In an ideal case, the I and Q A-lines would be measured at identical sample positions. However, if A-lines A1 and A2 in this example are used to construct a complex fringe, an error in the phase relationship may occur as a result of beam displacement between A-lines; a similar situation would occur if A-lines A2 and A3 were used. To reduce this error, a new (I) A-line may be constructed from the measured A-lines A1 and A3 by interpolation. This interpolated A-line approximates what would have been measured for the I A-line at location A2 (labeled in FIG. 6 as "A-line interp."). The complex fringe is then generated from the measured Q A-line (A2) and the interpolated I A-line formed from A1 and A3.

To implement A-line interpolation, in various embodiments the OSWSS and the data acquisition systems may be synchronized with one another so that A-lines are phase-stable. Without phase stability, errors may result from interpolation between A-lines A1 and A3 due to an unknown phase shift between these A-lines. Phase synchronization allows direct interpolation without phase compensation of the A-lines. One embodiment of phase synchronization scheme is shown in FIG. 5, which depicts a controller/signal generator that is electronically coupled to the OSWSS, the phase modulator, the detector(s), and the computer (e.g. which may be used for data collection and/or analysis).

The A-line interpolation may be determined in the fringe domain (i.e., on the captured fringe data), or it may be determined after FFT of the individual measured A-line fringes (i.e., on the complex data generated by the FFT operation).

Phase Modulation Between Successive Frames

The phase modulation approach disclosed above does not necessarily need to be implemented in adjacent A-lines. For some imaging systems, it may be optimal to phase modulate between frames, where a frame may be a collection of A-lines, for example along a particular direction such as the x-direction, that may be used to generate a continuous image. Accordingly, the beam may be scanned repeatedly in a first direction on the sample (e.g., x-direction) while also being translated in a second, typically orthogonal, direction (e.g., y-direction).

Figure 7:
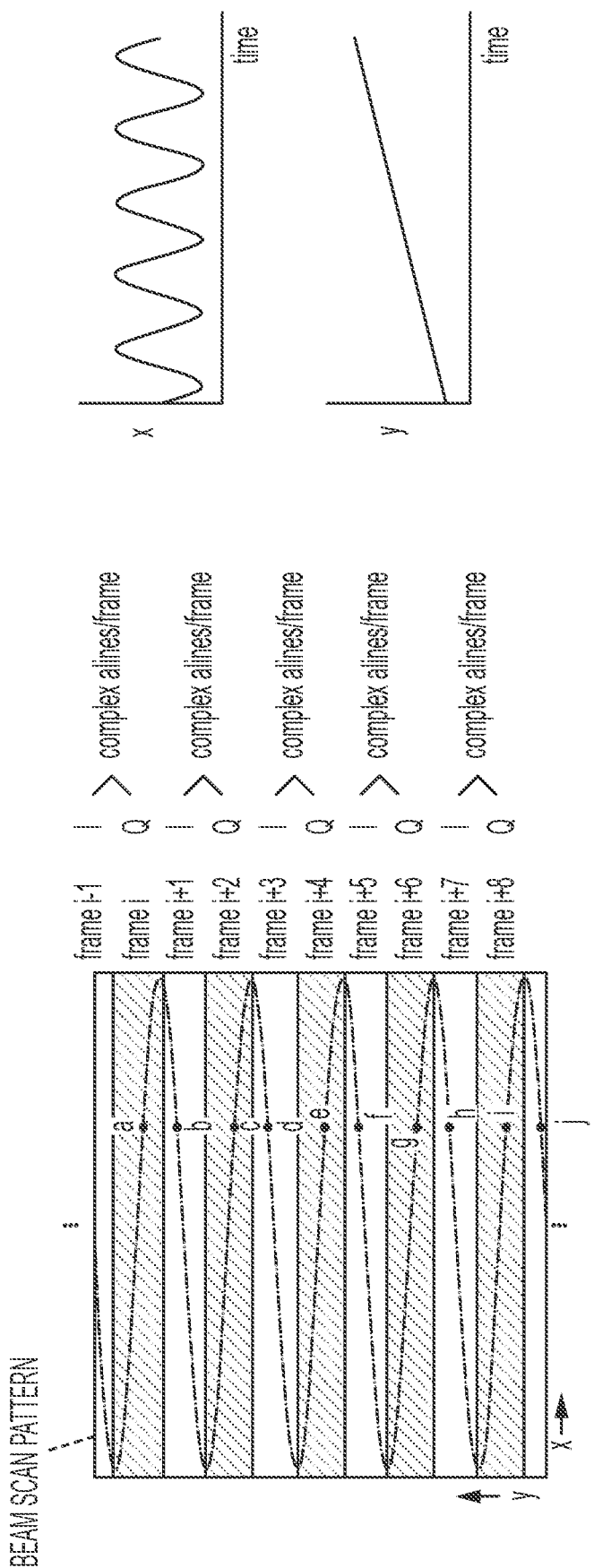
FIG. 7 shows an embodiment of a beam scan pattern superimposed on a phase modulation pattern (left panel) for a series of frames i−1 to i+8 (where a frame may include a series of A-line scans), where each alternating frame has a different phase (e.g. 0 degrees or 90 degrees), and a schematic diagram of the x- and y-positions of the scan as a function of time (right panel).

As shown in the left panel of FIG. 7, a sinusoidal scanning in the x-direction is used, where every other frame has a 0 degree phase shift applied for generating in-phase (I) data, and the other A-lines have a 90 degree phase shift applied for generating quadrature (Q) data. If the scanning along the y-direction at a constant velocity is sufficiently slow, the adjacent frames sample sufficiently similar locations such that data from these frames can be combined to generate a complex frame. For example, the A-lines at locations b and c can be used where b and c are at the same x-position but are at slightly offset y-positions. The right hand panels in FIG. 7 describe the x- and y-scan positions versus time.

Figure 8:
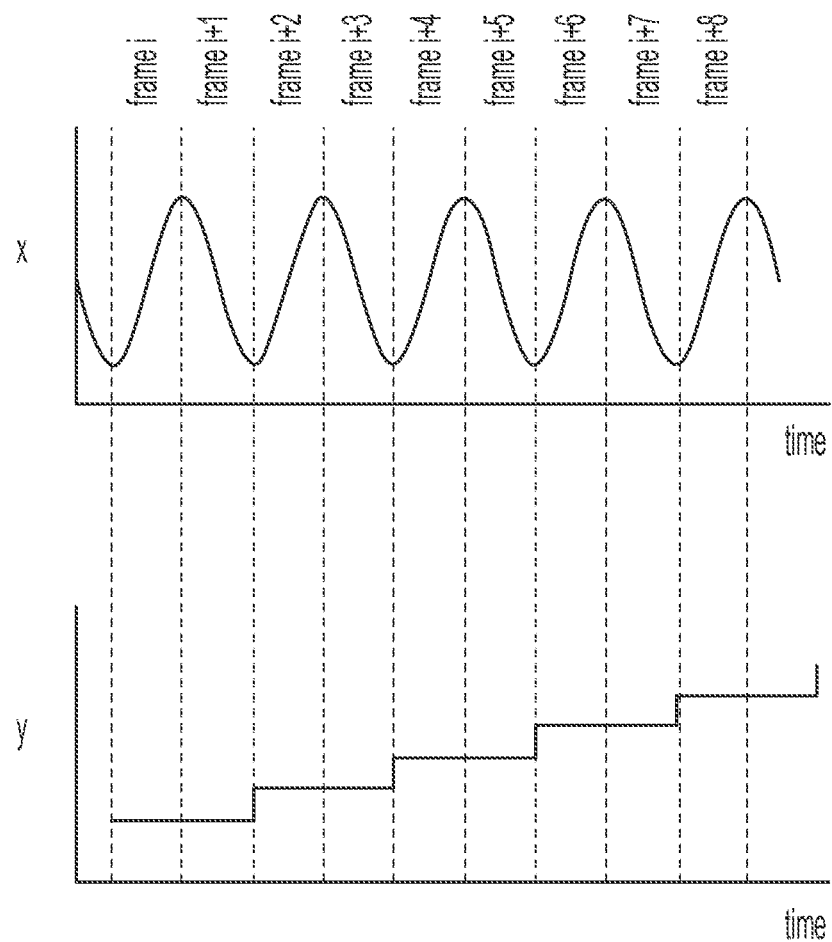
FIG. 8 shows x- and y-positions of an alternative embodiment to that shown in FIG. 7 in which the y-position is moved in a stepwise manner after two frame scans (e.g. one with the phase at 0 degrees and one with the phase at 90 degrees) in order to obtain complex demodulation data that is correctly registered.

Alternately, shown in FIG. 8 the y-scanning may be modified so as to maintain the y-position constant during a two-frame acquisition such that the A-lines from these two frames have the same y-position, and therefore the A-lines have the same x- and y-positions, which is beneficial for constructing the complex A-line/frame. This is illustrated in FIG. 8 where the positions in x and y are shown versus time. Here, frame i and frame i+1 could have phase shifts of 0 degrees and 90 degrees, respectively, and could be used to generate complex fringe/A-line/frame data, where all data has the same y-position.

The following non-limiting examples further illustrate embodiments of the invention disclosed herein.

Alternating A-Line Demodulation

Figure 9:
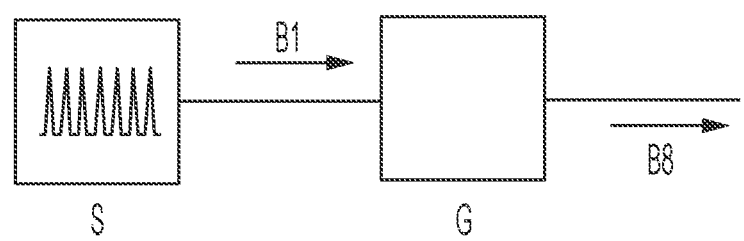
FIG. 9 shows a wavelength stepped light source (S) which produces a wavelength swept frequency comb which produces a beam B1 that is amplified by gain medium G and emitted as output beam B8.

FIG. 9 depicts a wavelength stepped light source (S) which produces a wavelength swept frequency comb, having a frequency comb free spectral range (FSR) and which may or may not have pulsation in the time domain with a pulse repetition rate ($f_P$) depending on the FSR and sweep speed. The light source S produces a beam B1 which is amplified using a gain medium (G) made of a semiconductor optical amplifier, a booster optical amplifier, or another type of gain medium, leading to an output beam B8.

Figure 10:
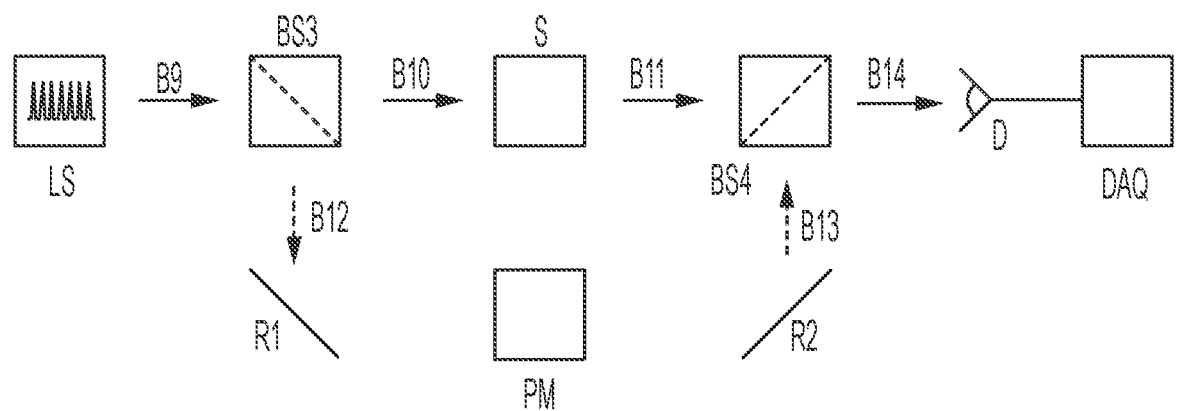
FIG. 10 shows an embodiment of a Mach-Zehnder interferometer for carrying out embodiments of the invention using a light source LS such as that shown in FIG. 9, where panel A shows an embodiment based on free space optics and panel B shows an embodiment based on fiber optics.
Figure 10:
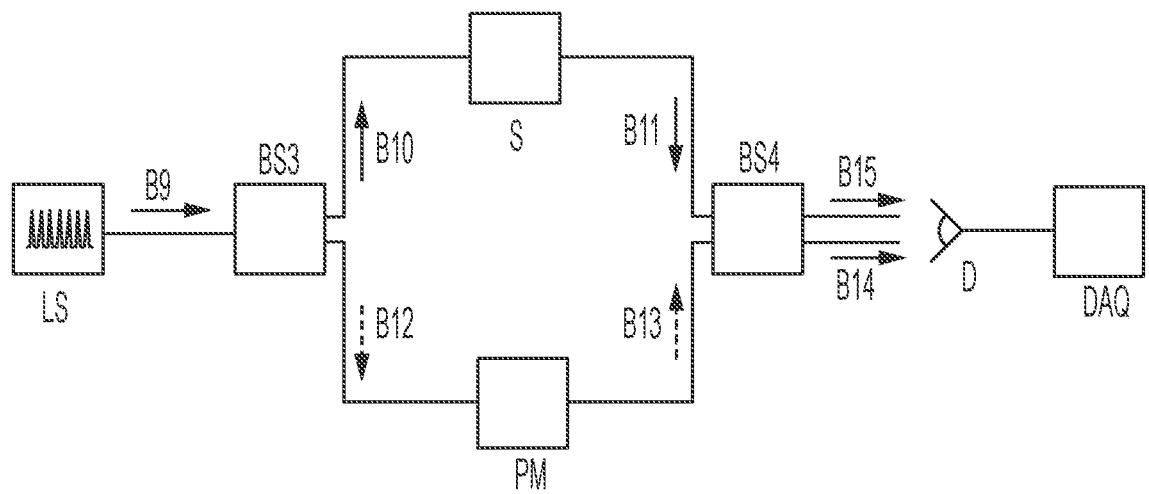

FIG. 10 illustrates a Mach-Zehnder type interferometer that may be implemented using free space optics (FIG. 10, panel A) or a fiber arrangement (FIG. 10, panel B). Other interferometer types (e.g. Michelson) can also be applied. The light source LS in either panel A or panel B of FIG. 10 represents the output beam B8 in FIG. 9. Beam B9, emitted from LS, is directed to the interferometer input where it is split into two paths of approximately equal length using a beam splitter (BS3). B10 is directed towards a sample S. The backscattered light from the object of interest is then directed towards the interferometer output (B11). In the reference arm, beam B12 is directed towards a phase modulator (PM). In this example, PM applies a phase shift of zero or π/2 (90 degrees) at a frequency of half the laser repetition (A-line) rate, meaning that every other group of pulses corresponding to an A-line has a phase shift of 0 degrees or 90 degrees applied in the reference arm. Alternatively, the laser repetition rate may be an integer multiple of the PM frequency, $f_L=nf_{PM}$ (n≥2) (e.g. the phase may change on every 3rd, 4th, 5th, ... or nth A-line). The beam after the PM (i.e. beam B13) is directed to the interferometer output to interfere with beam B11 after being combined by BS4. The output beam B14 is then detected by a photodiode D. Alternatively, a fiber-based interferometer shown in FIG. 2B readily allows balanced detection due to a phase shift of 7C between output beams B14 and B15. The detected signal is digitized using a data acquisition board or real time oscilloscope (DAQ) at a sampling rate $f_S$. Several wavelength sweeps (A1, A2, ..., An) may be acquired to form a 2-dimensional or 3-dimensional image.

During acquisition, the sample arm beam B10 is scanned across in a lateral or transverse direction to form a 2-dimensional image (B-scan), for example as shown in FIG. 6. The phase modulator PM in this instance induces a phase shift between alternating A-lines of zero and π/2 (90 degrees) that form the I and Q components, respectively, of the complex interferometric signal. In certain embodiments, the beam scanning speed is adjusted so that successive A-lines are spatially separated by a beam step size of ¼ of the beam diameter or less.

For a beam step size much smaller than the beam diameter, the complex interferometric signal (analytic signal) may then be obtained as Sc=I+√−1Q or Sc=I−√−1Q, which yields suppressed complex conjugate terms after Fourier transformation in the depth domain.

For beam step sizes approaching the beam diameter, the detected signals may be increasingly uncorrelated, leading to reduced reduction of complex conjugate terms. Complex valued interpolation may be applied, as discussed above, between An and An+2 (i.e. between neighboring I A-lines and/or neighboring Q A-lines) to obtain corrected (interpolated) I' or Q' components at the spatial location of their Q or I counterpart, respectively. In this case, the complex interferometric signal is then formed as Sc=I+√−1Q' or Sc=I−√−1Q' or Sc=I'+√−1Q or Sc=I'−√−1Q.

Alternating Sample Point Demodulation for Continuous Wave (CW) or Quasi-CW Laser Operation In this embodiment, a light source such as that shown in FIG. 9 is input to an interferometer such as that shown in panel A or panel B of FIG. 10. As indicated above, the output beam B14 is detected by a photodiode D or, alternatively, a fiber-based interferometer shown in FIG. 10 panel B readily allows balanced detection due to a phase shift of 7C between B14 and B15. The detected signal is digitized using a data acquisition board or real time oscilloscope (DAQ) at a sampling rate $f_S$. In various embodiments, the sampling rate may be adjusted to twice the pulse repetition rate, $f_S=2f_P=2v/FSR$, where v is the sweep speed in Hz/s. The phase modulator PM is set to modulate the phase of the interferometric signal between zero and π/2 (90 degrees) at a rate that is equal to the pulse repetition rate and half the digitizer (DAQ) sampling frequency.

Figure 11:
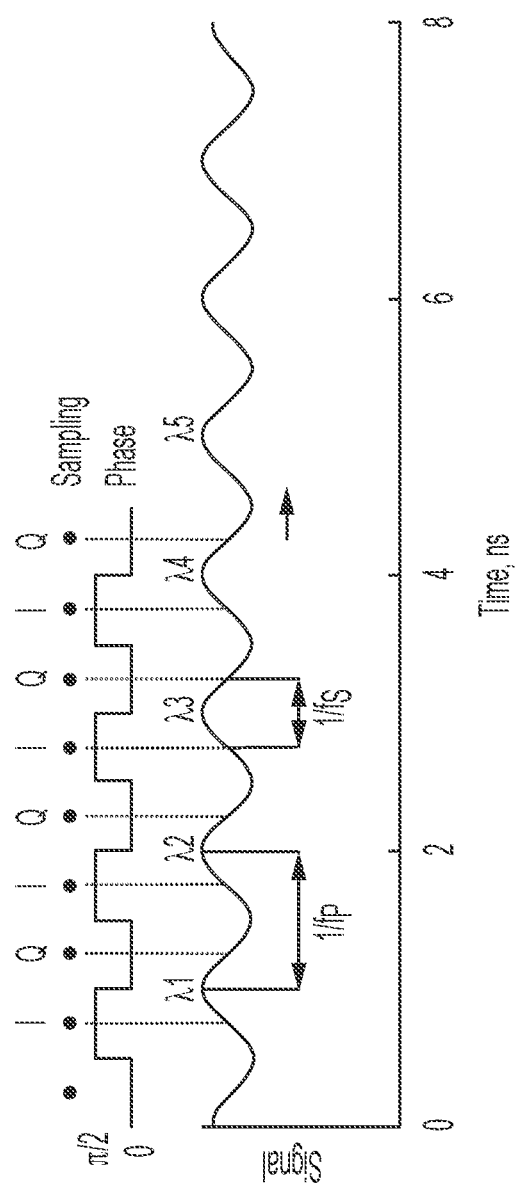
FIG. 11 shows an embodiment of a phase modulation pattern for use in conjunction with a continuous wave (CW) or quasi-CW laser.

The relative phase of the sampling and phase modulation with respect to the pulses can be adjusted as depicted in FIG. 11. In this embodiment, $\lambda_n$ (n=1, 2, 3, 4, 5, . . . ) represents the individual 'underlying' narrow linewidth comb lines in the spectral domain. Two points are acquired per pulse, phase shifted by $\pi/2$ with respect to each other, to form the I and Q component of the complex interferometric signal, $S_c = I + \sqrt{-1}Q$ or $S_c = I - \sqrt{-1}Q$.

Alternating Sampling Point Demodulation for a Pulsed Laser Output

Figure 12:
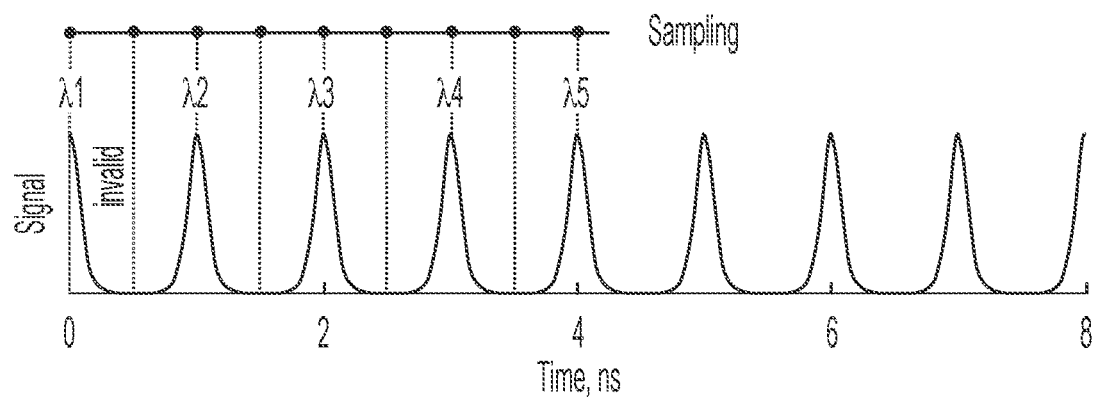
FIG. 12 shows an embodiment of a phase modulation pattern for use in conjunction with a pulsed laser output, where panel A shows a sampling pattern with the pulsed laser output, panel B shows a sampling and phase modulation pattern in conjunction with the pulsed laser output and a delayed copy of the pulsed laser output, and panel C shows a sampling and phase modulation pattern in conjunction with the pulsed laser output and a further delayed copy of the laser output.
Figure 12:
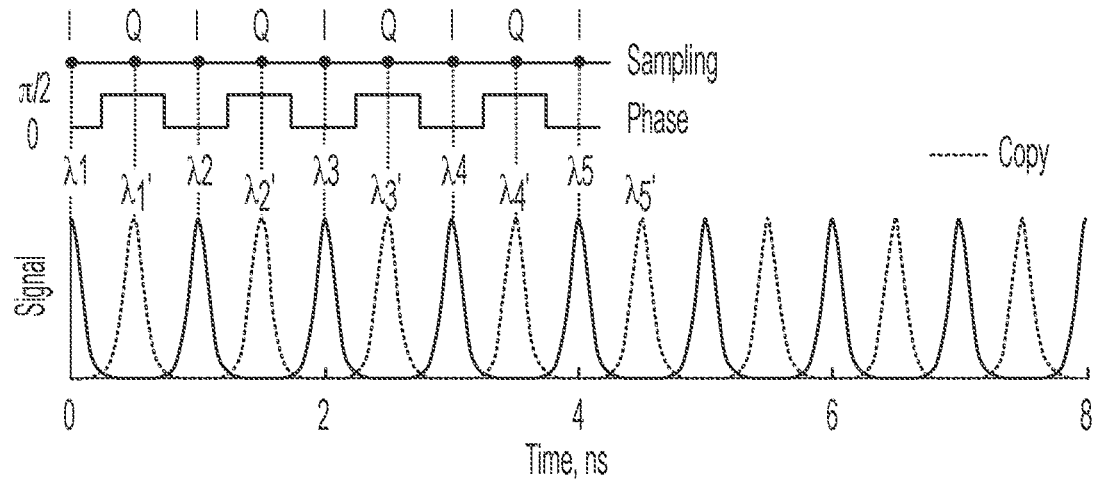
Figure 12:
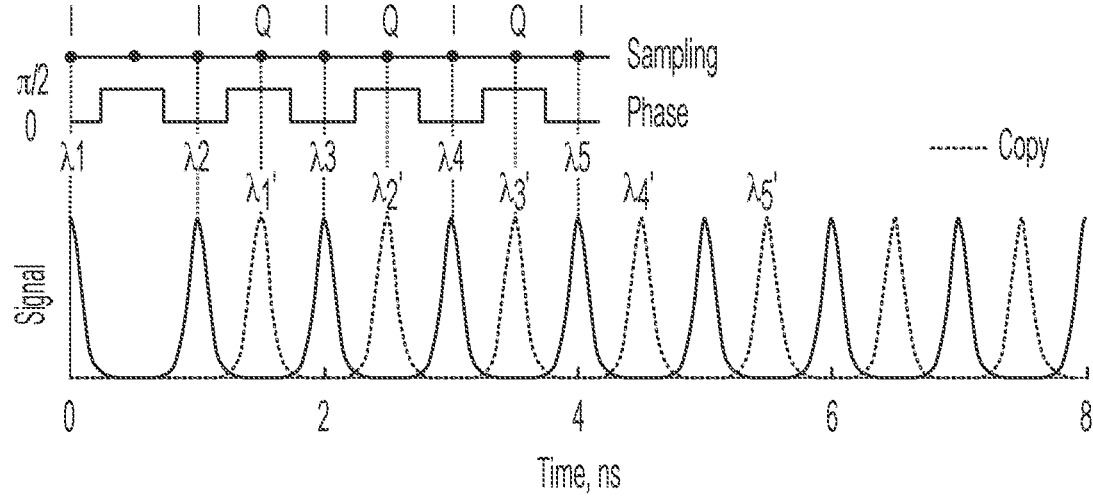

In the case of a pulsed laser output, sampling between pulses may lead to invalid I/Q components, as depicted in panel A of FIG. 12, which may become more pronounced for pulses having a low duty cycle. In FIG. 12, $\lambda_n$ represents the individual 'underlying' narrow linewidth comb lines in the spectral domain. In this embodiment, the problem of sampling between pulses may be addressed by generating a pulse train replica and pasting this replica into the low duty cycle region of the original pulse train, as shown in panel B of FIG. 12. In other words, the same comb line ($\lambda_n$) and pulse is copied and pasted ($\lambda_n'$) with a delay and is thus sampled by alternating sampling points, each $\pi/2$ phase shifted with respect to each other.

Figure 13:
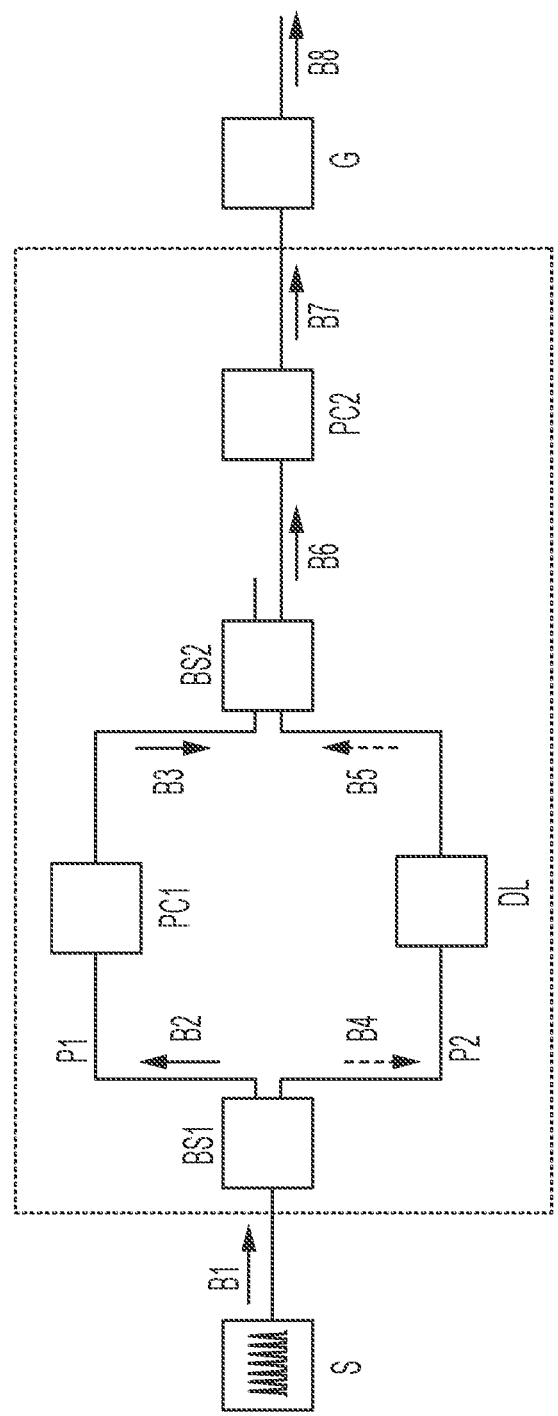
FIG. 13 shows an embodiment of a wavelength stepped light source (S) coupled to optical components that combine the output of the source S with a delayed copy of the source S.

FIG. 13 shows an embodiment of a wavelength stepped light source (S) coupled to optical components that combine the output of the source S with a delayed copy of the source S to produce a signal output such as that shown in panels B or C of FIG. 12. The wavelength stepped light source S of FIG. 13 produces a wavelength swept frequency comb having a frequency comb free spectral range (FSR). Pulses of source S have a pulse width and pulse repetition rate that depends on the FSR and sweep speed. The light source S produces a beam B1 which is split into two paths (P1, P2) by a beam splitter/coupler (BS1). Beam B2 is directed to a polarization controller (PC1) that ensures equal polarization between P1 and P2. After PC1, beam B3 is directed to a beam splitter (BS2) that combines P1 and P2. Beam B4 is directed to a delay line (DL) that induces a time delay between P1 and P2. Without the delay line DL, paths P1 and P2 would have equal lengths and thus the copied pulses would simply be recombined to form a string of pulses that is equivalent to the output of source S.

In various embodiments, the time delay induced by DL may correspond to half the inverse of the pulse repetition rate, $1/(2f_P)$, delaying the copied pulse string (dashed lines in panel B of FIG. 12) by half a pulse cycle. This principle can be applied more generally by pasting $\lambda_n'$ at other regions of signal void (between pulses) as depicted in panel C of FIG. 12 (where the pulses are delayed by one and a half pulse cycles). The applicable time delay can be written more generally as $n/(2f_P)$, where n is an odd integer. After delay loop DL, the beam B5 is directed to beam splitter BS2 which combines beam B3 with beam B5. This produces two interleaved pulse trains at the output of BS2. Both beams pass a polarization controller (PC2) before being amplified by a gain medium G. The output beam B8 is then directed to an interferometer such as those shown in panels A and B of FIG. 10 for imaging, where the arrangement of FIG. 13 is light source LS emitting beam B9. In various embodiments, the sampling rate may be adjusted to twice the pulse repetition rate, $f_S = 2 f_P = 2v/FSR$, where v is the sweep speed in Hz/s. The phase modulator PM modulates the phase of the interferometric signal between zero and $\pi/2$ at a frequency of the pulse repetition rate and half the sampling rate of the digitizer (DAQ). The I and Q components are extracted from the individually sampled pulses to form the complex interferometric signal $S_c = I + \sqrt{-1}Q$ or $S_c = I - \sqrt{-1}Q$.

In the Alternating Sample Point Demodulation for Continuous Wave (CW) or Quasi-CW Laser Operation embodiment or the Alternating Sampling Point Demodulation for a Pulsed Laser Output embodiment, the phase modulation frequency and sampling rate may be similar or equal to the analog bandwidth of the photodiode D and digitizer DAQ. However, frequencies near the bandwidth limit are subject to an additional frequency dependent phase shift which may lead to incorrectly measured I, Q components as the interferometric signal experiences a phase shift from PM and a depth dependent phase shift from the detection electronics. This in turn may cause insufficient suppression of the complex conjugate artefacts. In certain embodiments, a correction for this additional phase shift may be made by including a depth dependent calibration. The corrected quadrature components (I and Q) can be written as $S_c = I + \sqrt{-1}Q = I + \sqrt{-1}Q'\alpha$, where Q' is the measured phase shifted component of the complex fringe and $\alpha$ is a complex correction factor that is obtained at the location of the residual complex conjugate component by applying the condition $0 = I + Q'\alpha$.

Correction of Phase Errors

Certain embodiments of circular-ranging optical coherence tomography (CR-OCT) systems help to reduce the number of measurements required to image across extended depth ranges in most applications. However, in certain cases the imaging system architectures used in these embodiments, while being sufficient to demonstrate the core principles of the CR approach, may be unstable and may be limited to operation at 1.55 μm. Therefore, embodiments of a revised CR-OCT architecture are presented which improve operating stability and/or translate the technique to other wavelengths bands including the more common 1.3 μm range imaging band. In various embodiments, the long lengths of chromatically dispersive fibers used when employing a stretched-pulse mode-locked (SPML) laser source may be replaced by a single continuous chirped fiber Bragg grating (CFBG) design, a modification which not only shifts the operating wavelength to a window from 1260-1360 nm but also significantly stabilizes the laser operation. Further, embodiments of an active quadrature demodulation scheme using a lithium niobate phase modulator have been implemented in place of polarization-based optical quadrature demodulation circuits, which may be sensitive to environmental factors. The performance of these modified systems has been quantified and imaging examples are provided which have operating speeds of 7.6 MHz, a sweep bandwidth of 100 nm, a coherence length of 4 cm, and a circular ranging depth that is adjustable over a wide range, which in some embodiments may range between 100 μm and 4 mm. In various embodiments, the combination of one or more of the stability and simplicity of the CFBG-SPML laser, the operation at 1.3 μm, and/or the active quadrature demodulation schemes define a more compact, stable, and straightforward to operate CR-OCT system, which may serve to broaden the exploration of CR-OCT techniques across both medical and non-medical applications.

Circular-ranging optical coherence tomography (CR-OCT) can solve two technical hurdles confronting conventional Fourier-domain OCT approaches. First, when attempting to use FD-OCT methods to interrogate extended depth ranges at high depth-scan rates, a large number of measurements (i.e., digitized samples) are required in a short duration. This can impose high, often unreachable, requirements on the electronic bandwidths of the detection, digitization, transfer, and processing modules in OCT systems.

This is especially challenging in applications that require continuous (as opposed to burst-mode) imaging. CR-OCT overcomes this barrier by leveraging the inherent sparsity in the depth-resolved profiles in most applications. Specifically, the depth space is circularly folded such that only a small circular depth range needs to be acquired. This circular depth range can be set to approximate the depth extent of the signals reflected from the sample, typically in a range of 0.5-2 mm but not restricted to this range. Yet the sample can be located across a broader physical depth range that may span many centimeters. In short, CR-OCT enables an efficient sampling of the sample signals by discarding the absolute position information of the sample.

The second technical hurdle that can be overcome by adoption of CR-OCT methods is that of imaging source speed. Conventional Fourier-domain OCT lasers are comfortably used in the 100-400 kHz range and can be made to operate beyond 1 MHz through optical buffering as a workaround to mechanical limits in critical swept-wavelength filters. CR-OCT is based on the use of a frequency comb source. The ability to use discretely stepped rather than continuous swept wavelengths opens new opportunities in extremely fast, >10 MHz source designs. Prior CR-OCT imaging results were obtained using a stretched-pulse mode-locked design based on intracavity dispersion. Although sources such as these have served to demonstrate the core CR principles, they are complex and unstable; on the other hand, more elegant frequency comb laser sources based on chirped fiber Bragg gratings (CFBGs) having a theta-cavity architecture have been reported but so far imaging with a frequency comb CFBG-SPML source has not been demonstrated. In prior works, CR-OCT was used to capture tissue signals with measurement compression factors ranging from 10-42 at A-scan rates of up to 22 MHz.

In certain embodiments of CR-OCT systems, the source and the interferometer may require frequent adjustment and calibration to maintain high performance. A contributor to source instability has included the use of long lengths (>10 km) of dispersive fibers. The use of long dispersive fibers can sensitize the laser cavity resonance frequency to temperature and, because the entire system is phase-locked, changes to the laser drive frequency may need to be propagated to beam scanning and digitization clock sources. A more stable laser design would dramatically simplify operation in both research and pre-clinical/clinical environments. To achieve the circular folding of depth space that defines the technique, complex fringe signals including in-phase and quadrature signals are detected. In certain embodiments, a particular polarization-based quadrature demodulation circuit may be used. This circuit in combination with a correction algorithm may provide high performance demodulation, but the correction parameters may have to be frequently remeasured through a fairly involved calibration procedure. Finally, a third deficiency of certain designs, unrelated to stability, are their inability to translate to other imaging wavelengths such as 1.3 μm or 1.0 μm. This was imposed by the use of matched positive and negative dispersive fibers, which are broadly available only above 1.5 μm. To enable the technique to be studied in clinical settings and to enable a more robust adoption of CR techniques, a simplified, more stable laser and interferometric architecture operating at conventional imaging wavelengths is needed.

The CR-OCT technique/system operates on complex interference fringes to achieve circular ranging. Unfortunately, the use of frequency combs can generate RF errors that cause artefacts when imaging at multiples of the principal measurement range of the frequency comb free spectral range (FSR). To access the full depth range, use of the analytic (i.e. complex) interference signal is generally required. To avoid overlap of artefacts, signal folding is performed in a circular manner through the combination of a frequency comb optical source and the use of complex demodulation, i.e., the detection of in-phase (I) and quadrature (Q) fringe signals that resolve the sign of the measured delay, as disclosed herein. Complex demodulation methods have been explored in traditional Fourier-domain OCT to extend the imaging range by a factor of two through use of the positive and negative delay spaces. Passive methods based on optical quadrature circuits and active methods based on dynamic phase modulation have been demonstrated. For traditional OCT, complex demodulation is optional as the entire depth signal can be placed in either the positive or negative delay space. The same strategy can be applied to optical subsampling but limits the depth range to the fundamental frequency comb order due to aliasing beyond the principal measurement range. Therefore, circular ranging is enabled by the combination of optical subsampling and complex demodulation. That is, in the case of CR-OCT the complex signal is not optional but essential. In certain CR-OCT demonstrations, a passive method has been employed. While this has provided the required performance, there are advantages in active methods that reduce digitizer channel counts and avoid the need for environmental stability. We have demonstrated circular ranging by frequency shifting using an acousto-optic-modulator and a Fourier-domain mode locked frequency comb laser. This method can provide stable, single channel, intra A-line complex demodulation but may be limited to laser repetition rates up to ~3 MHz. Thus, described herein is the extension of active demodulation schemes to CR-OCT systems. In particular, highlighted are embodiments of CR-specific alterations for efficient, high-speed, and stable methods based on a $LiNbO_3$ electro-optic modulator (EOM) by describing two inter A-line demodulation techniques. Moreover, to move the high speed of the CFBG-based SPML architecture to more relevant OCT wavelengths, a SPML laser at 1.3 μm is demonstrated for the first time, which provides a compact and stable SPML-based circular ranging system for OCT imaging.

Setup

Figure 14:
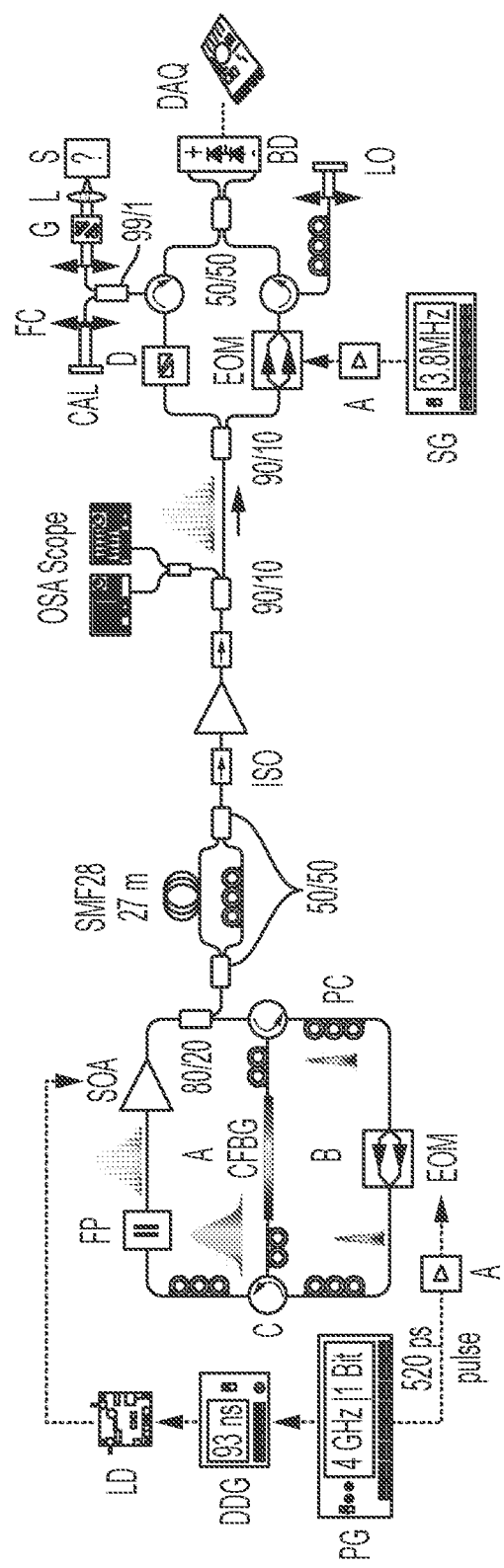
FIG. 14 shows a schematic of an SPML laser and circular ranging imaging system: LD, laser diode driver; DDG, digital delay generator; PG, pattern generator; A, amplifier; EOM, electro-optical modulator; PC, polarization controller; CFBG, continuous fiber Bragg grating; SOA, semiconductor optical amplifier; FP, Fabry-Pérot etalon spectral filter; C, circulator; PZT, Piezo actuator; PM, partially reflecting mirror; OSA, optical spectrum analyzer; VD, variable delay line; ISO, optical isolator; FG, signal generator; D, dispersion compensation; LO, local oscillator; CAL, calibration signal; FC, fiber collimator; G, galvanometer mirrors; L, lens; S, sample; BD, balanced photodiode; DAQ, data acquisition board.

FIG. 14 shows the optical configuration that includes the SPML laser and a Mach-Zehnder type interferometer. An electro-optic modulator EOM (MX1300-LN-10, Photline) was driven in resonance at a harmonic of the cavity round-trip time at 3.87 GHz. The 520 ps pulse was generated with an electrical signal composed of 1024 bits (32 words) using a pattern generator PG (PAT 5000, SYMPULS) that was amplified by an amp A (DR-PL-10-MO, iXblue), where a single bit corresponded to a 260 ps pulse. An additional signal generator (SG384, Stanford Research Systems, Inc.) was used to generate an external clock signal for the pattern generator. A continuous fiber Bragg grating (CFBG, Proximion) was placed between two circulators to access both normal and anomalous dispersion. The 9.5 m grating was designed to produce a linear group delay with respect to optical frequency over a continuous wavelength range from 1240 nm to 1340 nm ($\Delta\lambda$=100 nm). The dispersion at 1290 nm was ±930 ps/nm (98,000 ps/nm/km) corresponding to a sweeping time of 93 ns. By using the CFBG from both directions, we generated matched normal and anomalous dispersion from the same device. The CFBG-based SPML design is crucial for the implementation in the 1.3 μm range, where standard SMF has zero dispersion. The laser output was taken after the SOA using a 20% output tap coupler (labeled "80/20" in FIG. 14). To generate a frequency comb output, a fixed Fabry-Pérot etalon was used in the cavity that had a single pass Finesse of 12 and a continuously adjustable free spectral range (FSR). The etalon was constructed using two glass plates (Korea Electro-Optics Co., LTD.). Both plates had a planar surface with a reflectivity of 85% on one side and an angled surface on the other side to mitigate back reflections. The measured single pass Finesse was lower than the expected Finesse of 18, possibly due to surface irregularity and/or deviations from the set reflectivity. Note that this frequency comb was nested on top of the ~3.8 MHz frequency comb of the actively mode-locked laser cavity, where only the nested frequency comb is relevant for imaging. Within the CFBG passband, approximately 30% of the light is transmitted, creating three optical cavities (A, B, AB). To suppress light circulating in cavities A and B, we used SOA modulation (T160, Highland Technology) at a frequency given by the cavity AB roundtrip time, with an on-state determined by the CFBG dispersion (93 ns). The modulation was applied using a digital delay generator DDG (DG645, Stanford Research Systems) that was triggered by the pattern generator. The external clock generator, pattern generator, and digital delay generator were phase synchronized using a 10 MHz reference signal, with the clock generator acting as the master clock. The implemented configuration had a 38% duty cycle, which yielded a 3.8 MHz repetition rate at the laser output. The repetition rate was doubled to 7.6 MHz (76% duty cycle) using a delay line made of 27 m of SMF28, followed by post-amplification. The repetition rate can be further optimized to a maximum value of 10 MHz by reducing the cavity length or the number of bits used by the pattern generator. The laser repetition rate is a relative parameter that depends on duty cycle and sweep bandwidth. The sweep speed was 194 THz/µs and is an absolute measure of laser performance.

The interferometer was made of a reference arm that provided a local oscillator and accommodated a $LiNbO_3$ electro-optic phase modulator (EO Space). The EOM was designed for a wavelength region at 1.3 µm and was made of a polarizing waveguide (no integrated polarizer), had a bandwidth of 10 GHz, an insertion loss of 3 dB, and a $\pi$-voltage of 5.3 V. For modulations above 30 kHz, the electrical signal was amplified using a broadband amplifier (MTC5515, Multi-Link Techn. Corp.). Although the phase modulator is expected to have a $\pi$-voltage wavelength dependency, there was no noticeable effect on the quadrature detection (i.e., suppression) across the sweeping bandwidth. In the sample arm, a galvanometer (504 Hz, Thorlabs or 4 kHz, EOPC) enabled two-dimensional scanning (see below). Imaging was performed using a lens with focal length of 50 mm that offered a spot size of 41 µm. Dispersion matching in the sample arm accounted for waveguide dispersion from the EOM. Signals were acquired using a 1.6 GHz balanced detector and a 4 GS/s, 12 bit data acquisition board (AlazarTech, ATS9373).

Results

Figure 15:
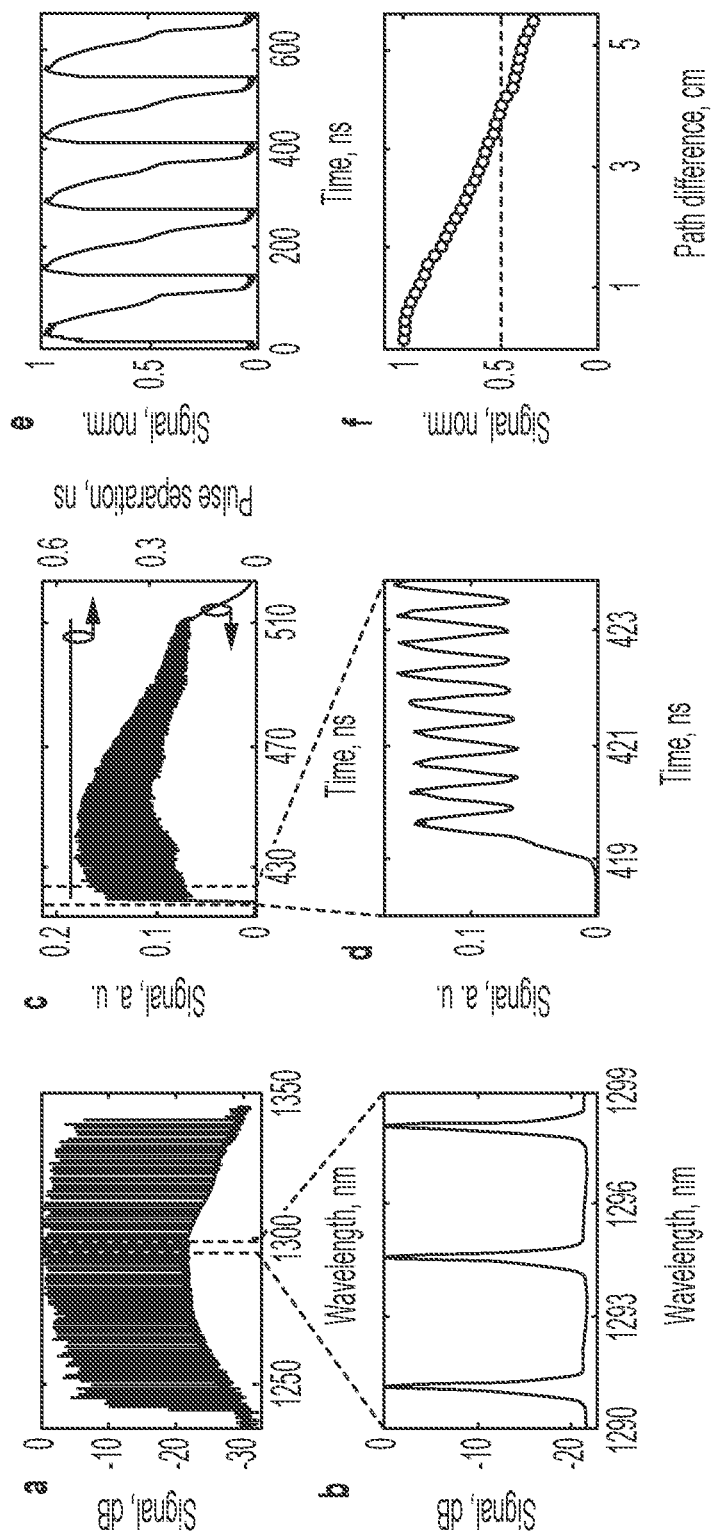
FIG. 15 Shows measured SPML laser performance, including panels showing: (a) Optical spectrum. (b) Magnified optical spectrum. (c) Time trace of a single sweep using a 260 ps electrical pulse. (d) Magnified time trace showing pulsation. (e) Time trace showing five sweeps. (f) Measured coherence length.

FIG. 15 panel (a) shows the laser output after post-amplification in the spectral domain, where the frequency comb structure is clearly visible. FIG. 15 panel (b) shows a zoomed view of the spectrum depicting a frequency comb with a FSR of 200 GHz. The etalon FSR can be continuously adjusted and demonstrated good performance up to 450 GHz. FIG. 15 panel (c) illustrates a time trace of a single sweep using a 260 ps (1 bit) electrical pulse and a FSR of 100 GHz. A zoomed view of the time trace is shown in FIG. 15 panel (d). The trace was recorded using a 35 GHz photo detector (1474-A, New Focus) and a 20 GHz sampling scope (HP 54120B). The underlying structure of the frequency comb is clearly visible in the form of pulsation. Because of the large linear chirp imposed by the CFBG, the pulses directly map corresponding optical frequencies of the frequency comb in the spectral domain. FIG. 15 panels (c) and (d) also depict a constant pulse separation time of 0.52 ns across the entire sweep. This is in excellent agreement with the inverse of the theoretical pulse repetition rate that is given by $f_P$=v/FSR, where v is the sweep speed (i.e., 194 THz/µs). This demonstrates a linear sweep that does not require linearization or an acquisition clock. Moreover, the measured optical pulse width ranged between 300 ps and 470 ps, which is broader than the 260 ps electrical pulse width of the pattern generator. This suggests spectral broadening of optical pulses due to gain saturation and pulse widths comparable to the carrier lifetime. A train of five sweeps is shown in FIG. 15 panel (e) demonstrating a 7.6 MHz repetition rate with a 76% duty cycle at a sweep speed of 194 THz/µs. The trace was recorded using a 520 ps electrical pulse at the EOM and a 2 GHz real-time oscilloscope (Tektronix, MSO5204). Pulsation was not observed in this case due to a pulse width similar to the inverse of the pulse repetition rate and reduced digitizer bandwidth. Finally, the measured coherence length of the laser after post-amplification is shown in FIG. 15 panel (f). It shows a 6 dB signal fall-off at an optical path difference of 4 cm.

Active, High-Speed Complex Demodulation

In the following, we describe two active, inter A-line demodulation techniques using a $LiNbO_3$ phase modulator. Active phase modulation based on waveguide-based lithium niobate devices provides a straightforward and highly configurable method to modulate phase and operates comfortably in the GHz range.

Frame Demodulation

Figure 16:
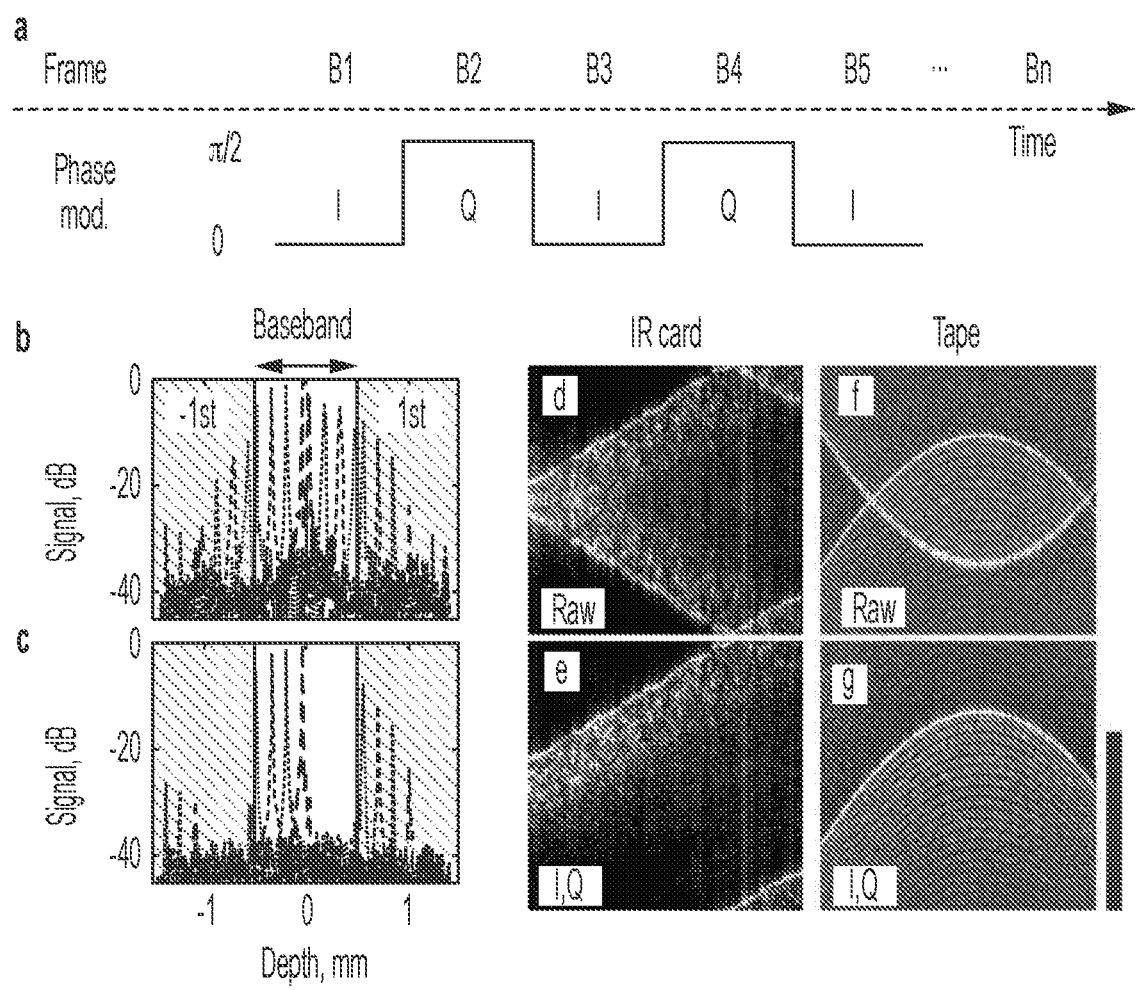
FIG. 16 shows frame demodulation, including panels showing: (a) Schematic of frame demodulation. (b),(c) Artefact suppression for mirror signals across the baseband showing the raw, dispersion compensated signals (b) and I,Q demodulated signals (c). FSR=150 GHz. The −1st, baseband, and 1st order signals are indicated. (d),(e) Imaging of an IR card showing the raw, dispersion compensated image (d) and I,Q demodulated image (e). (f),(g) Imaging of adhesive tape showing the raw, dispersion compensated image (f) and I,Q demodulated image (g). A FSR of 100 GHz was used during imaging. Scale bar corresponds to 1 mm.

Inter A-line frame demodulation acquires quadrature components from two frames by phase modulating alternating B-scans as shown in FIG. 16 panel (a). This method has been challenging previously due to slow imaging speeds with frame rates of less than 100 Hz and due to the need for high phase stability. The high repetition rate of the SPML laser allows frame rates in the kilohertz range where environmental fluctuations and vibrations from the microscope are reduced and more manageable. The quadrature components are extracted from recorded odd and even B-scans to form a complex signal as $S(x,z)=S_I(x,z)+S_Q(x,z)$, with $S_I(z)=FFT\{A_I(\omega)\}$ and $S_Q(z)=FFT\{\sqrt{-1}A_Q(\omega)\}$, where $A_{I,Q}(\omega)$ are A-lines within the I and Q B-scans and co is the angular optical frequency. A resonant scanner was employed that had a resonance frequency at 3908.45 Hz (PLD-1S, EOPC). The resonant scanner frequency was slightly detuned from its mechanical resonant to 3908.17 Hz to match an integer of the laser repetition rate for synchronization, providing 1932 A-lines per scanning cycle. The phase modulation frequency was adjusted to half the frame rate, $f_{PM}$=1.95 kHz. The sampling rate was adjusted to $f_s$=3.87 GS/s, which conveniently matched the pattern generator clock rate, yielding 389 points per A-line and a Nyquist depth of 1.5 mm, given by $z_{NQ}$=c fs/(4v). FIG. 16 panels (b) and (c) show point spread functions (PSFs) across the baseband range. A FSR of 150 GHz was used which had a principal measurement range, $L_B$=c/(2FSR), of ±0.5 mm. Theoretically, this only required a sampling rate of $f_s$=1.29 GS/s, considering $f_s$=2v$L_B$/c. However, to also demonstrate first order artefact suppression, the optical Nyquist frequency was deliberately oversampled. FIG. 16 panel (b) shows raw signals after numerical dispersion compensation, while FIG. 16 panel (c) shows the depth signals after I, Q demodulation. A suppression of approximately 40 dB is visible for the baseband as well as the ±1st frequency comb order. Note that the measured suppression was limited by the system noise floor. Complex demodulation is demonstrated by imaging an IR card (FIG. 16 panels (d) and (e)) and adhesive tape (FIG. 16 panels (f) and (g)). A FSR of 100 GHz ($L_B$=1.5 mm) was used during imaging. Only the baseband range is plotted in the images. The tape sample was highly transparent. The structure seen above the sample surface in FIG. 16 panel (g) corresponds to the 1st frequency comb order showing sample structure below the sample, and which is folded back into the baseband. Similarly, the IR card structure seen at the bottom, right corner of the image in FIG. 16 panel (e) is sample structure exceeding the upper baseband range and corresponds to the −1st frequency comb order. It is worth mentioning that because the scanning function of the resonant scanner is symmetric (sinusoidal), in certain embodiments one may phase modulate the forward and backward scan to obtain quadrature frames, thereby reducing the acquisition time by factor of 2. In that case, the scanner phase is expected to be critical and would require careful adjustment to assure frame correlation.

Phase Correction

Although the high frame rate of the resonant scanner and phase stability of the SPML laser substantially reduced phase noise between frames, small phase fluctuations were still observed which can lead to visible complex conjugate artefact residues. Even a small amount of axial motion (e.g. as little as ~3% of the wavelength such as ~40 nm motion when using a 1.3 μm imaging band) can cause artefacts. Examples of remaining artefacts are shown for the IR card and tape sample in FIG. 17 panels (a) and (b) (arrows labeled "cc"). The phase fluctuations were periodic and originated from mechanical microscope instabilities. Care must be taken when constructing a robust sample arm by isolating the microscope from sources of vibrations with frequencies higher than the EOM modulation (half the frame rate). The imperfect I,Q components were due to axial motion, which can be corrected.

Figure 17:
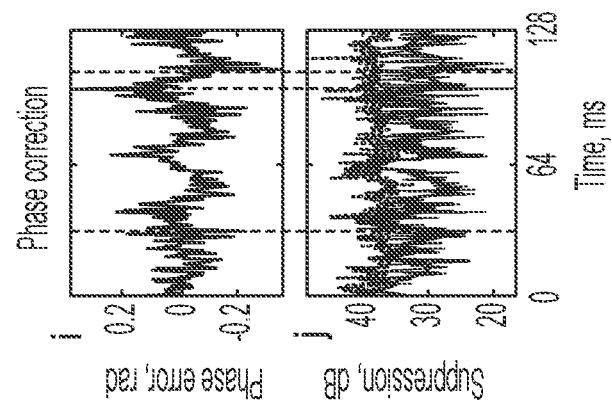
FIG. 17 shows an illustration of phase correction using an IR card (top row) and adhesive tape (bottom row), including panels: (a),(b) Images with remaining artefacts after I,Q demodulation (yellow arrow). (c),(d) Phase difference between phase modulated frames, $\varphi(x,z)=\arg\{S_I(x,z)S^*_Q(x,z)\}$. (e),(f) Phase histogram showing $\varphi$ occurrences from data shown in (c),(d). The histogram was used to obtain a global phase offset, $\Delta\varphi$, from the quadrature point. (g),(h) Phase corrected images. (i) Phase error (offset) from the ideal quadrature point for 251 continuously recorded frames. (j) Corresponding measured suppression due to the phase error in (i) before (lower black line) and after phase correction (upper red line). The thick lines show the averaged suppression using 5 frames. Scale bars correspond to 1 mm.
Figure 17:
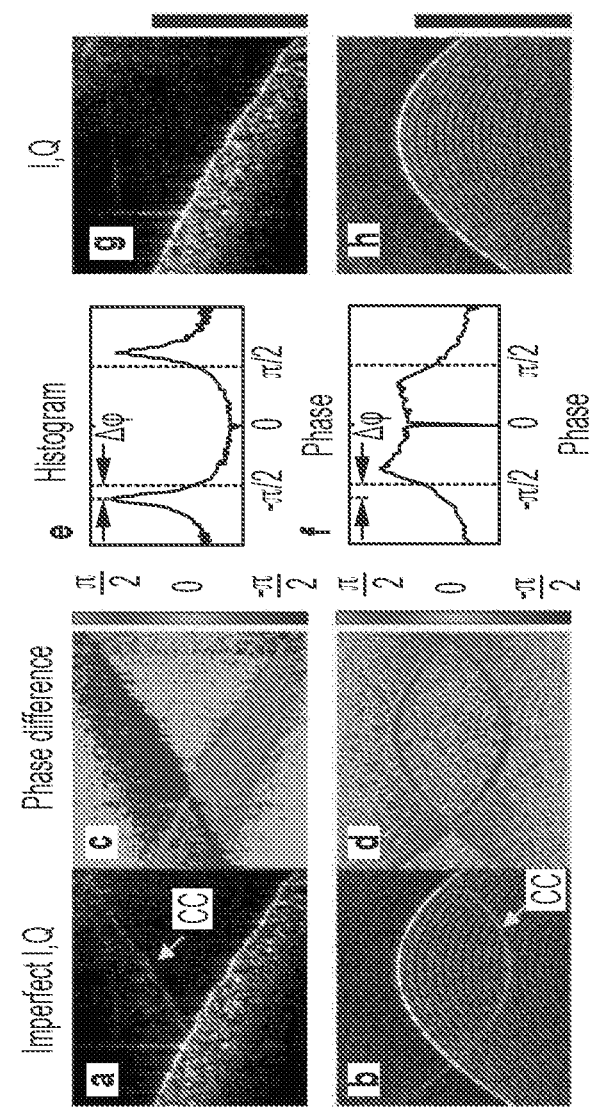

The phase difference between the complex I and Q frames, $\varphi(x,z)=\arg\{S_I(x,z)S^*_Q(x,z)\}$, is shown in FIG. 17 panels (c) and (d) for both the IR card and tape sample, respectively, where $S^*_Q(x,z)$ is the incorrect Q-valued frame that includes a phase error. The phase maps illustrate a constant phase difference affirming a global phase error across the B-scans. This can be better appreciated by plotting a histogram of the phase differences (FIG. 17 panels (e) and (f)), for example from the phase difference images as seen in FIG. 17 panels (c) and (d). The histograms clearly identify a mean phase difference that is higher than the ideal quadrature phase difference of π/2 for the IR card and lower than π/2 in the case of the adhesive tape. The offset of the mean phase difference from the quadrature point, $\Delta\varphi$, represents the global phase error preventing quadrature detection. During imaging, this phase error can be obtained from the one-sided histogram (either positive or negative side) of each frame and applied as a global phase correction factor, $S_Q(x,z)=S_Q(x,z)\exp(-i\Delta\varphi)$.

Thus, to summarize an embodiment of the phase correction scheme: the phase difference between the complex I and Q frames is given by $\varphi(x,z)=\arg\{S_I(x,z)S_Q^*(x,z)\}$, where $S_{I,Q}(z)=\text{FFT}\{A_{I,Q}(\omega)\}$ with $A_I(\omega)$ being an I-valued A-line and $A_Q(\omega)$ being an inaccurately Q-valued A-line within the frame. This phase map is used to obtain a global phase error across the B-scan (frame). First, the phase histogram is plotted from the phase map. Second, the one sided histogram (positive or negative side) is used to obtain the mean or maximum value of the phase difference. Third, the offset of the mean or maximum valued phase difference from the ideal quadrature phase difference (+π/2) is extracted. The offset from the quadrature point represents the global phase error, $\Delta\varphi$. The global phase error is applied to the complex valued frame as a global phase correction factor, $S_Q(x,z)=S_Q(x,z)\exp(-i\Delta\varphi)$. The corrected, artefact free frame is calculated as: $S(x,z)=S_I(x,z)+S_Q(x,z)$.

The additional computation time is minimal as the complex frames are directly available after Fourier transformation. The corrected images are shown in FIG. 17 panels (g) and (h). The highly overlapping structure of complex conjugate artefacts as well as 1st order signals of the tape sample represents a particularly challenging scenario. It leads to a large standard deviation of the phase in the histogram. Importantly, the phase error was identified and corrected. FIG. 17 panel (i) shows the phase error, $\Delta\varphi$, and the corresponding suppression (FIG. 17 panel (j)) for 250 frames over a time span of 128 ms before (black line) and after correction (red line). The overlaid thick lines show the averaged suppression using 5 frames. Three points, where the phase error exceeded 0.2 rad (3% of center wavelength), are highlighted by vertical dashed blue lines. The time varying phase error yielded imperfect I,Q components that reduced suppression down to 20 dB. Global phase correction reduces suppression to approximately 40 dB, corresponding to the system noise floor.

It is important to note that in case of large phase errors (in the order of π/2), the detected frames become degenerate and phase correction is not possible. The observed phase variations from microscope instabilities did not exceed 0.4 rad and never approached degeneracy. Sample motion, however, can lead to large phase errors and degenerate frames. Sample motion can also have a lateral component that cannot be corrected and thus, the correction method described here is better suited for static or slowly moving samples.

Imaging

Figure 18:
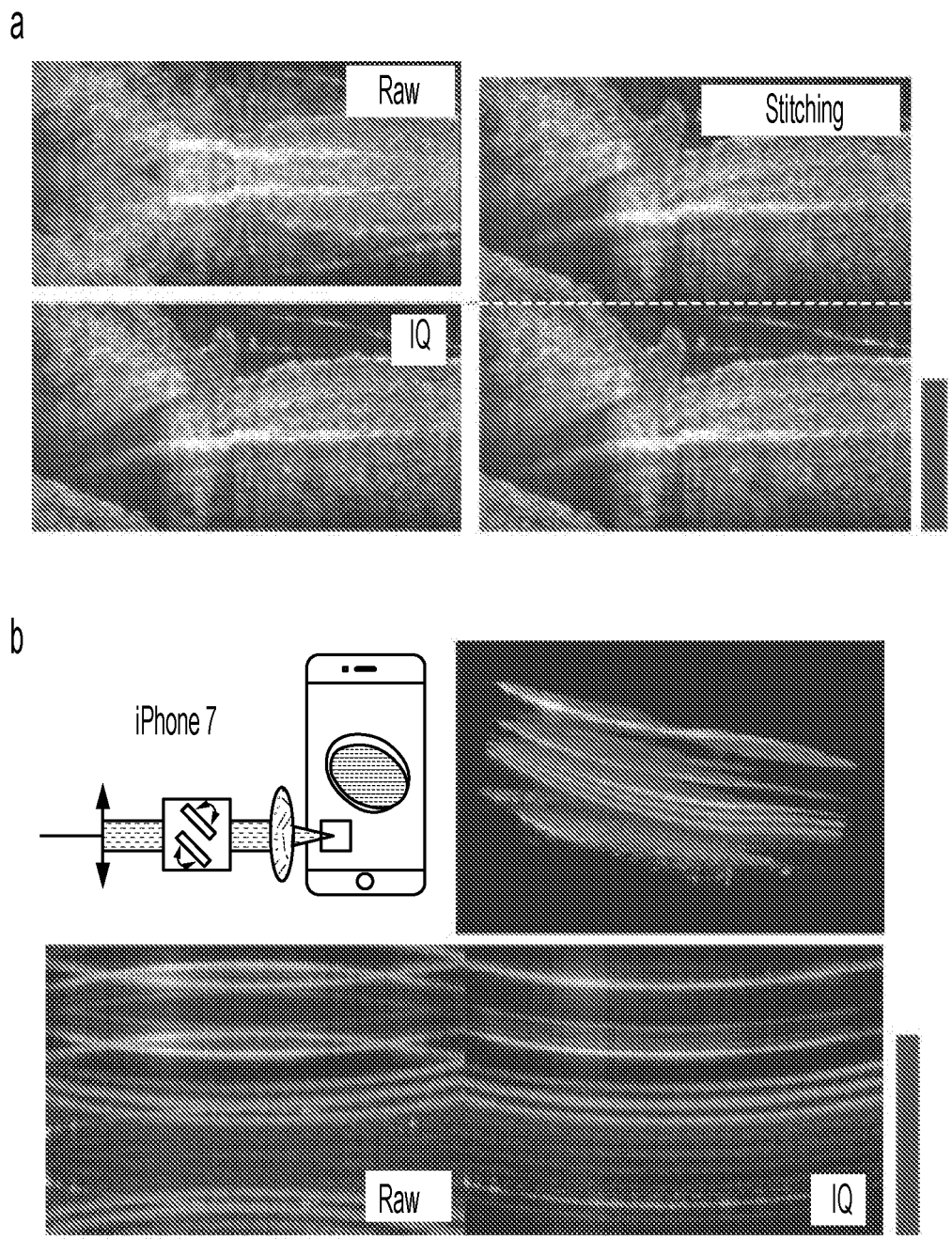
FIG. 18 shows imaging examples using frame demodulation, including panels: (a) Imaging of a human nail fold showing the raw, dispersion compensated image and the I,Q demodulated image. The demodulated image is stitched to make the borderless wrapping of structure exceeding the baseband range clearer. (b) Imaging of an iPhone 7 display showing the raw and I,Q demodulated image as well as a volumetric view. Distinct layers beneath the top glass plate are visible. Scale bars correspond to 1 mm.

An imaging example of a human nail fold is demonstrated in FIG. 18 panel (a). It is shown the raw, dispersion compensated image as well as the artefact free I,Q demodulated image. No phase correction was necessary. A FSR of 100 GHz was used and only show the baseband range is shown, i.e., $L_B$=1.5 mm. The I,Q demodulated image was stitched on top of itself in order to make the borderless wrapping of sample structure exceeding the baseband more clear. Moreover, FIG. 18 panel (b) shows imaging of an iPhone display. The raw and I,Q demodulated image as well as a rendered visualization of a volumetric image is shown, clearly highlighting numerous distinct layers below the surface. Because of missing literature, it was difficult to reliably identify the layers of an iPhone 7 display, which, however, is known to include a polarizing layer, liquid crystal and touch panel, a potential second polarizing layer, directional diffuser layers, a light guide plate with backlight and end reflector. This also demonstrates the strong suitability of SPML-based circular ranging by frame demodulation for industrial applications, where volumetric video-rate and long range imaging could be beneficial, including wide field-of-view material, display or paint inspection.

It is noteworthy that traditional OCT, using a continuously swept laser, with a 10 MHz A-line rate and 4 cm imaging range requires a sampling rate in the order of 100 GS/s. We compare this to circular ranging with a FSR of 100 GHz ($L_B$=1.5 mm) and sweep speed of 194 THz/μs (i.e., 10 MHz A-line rate with $\Delta\lambda$=100 nm, full duty cycle), which only requires a sampling rate of 2 GS/s as it is independent of coherence length (i.e., imaging range). This is a 50-fold reduction in sampling speed as well as data load slowing down signal and image processing. Depending on the application, the FSR may be increased to 200 GHz ($L_B$=750 µm), which could further increase the compression factor to 100. Moreover, with a 100% duty cycle, the 4 kHz scanning rate of the resonant scanner can be increased to at least 6 kHz, which would further reduce the phase error.

A-Line Demodulation

Figure 19:
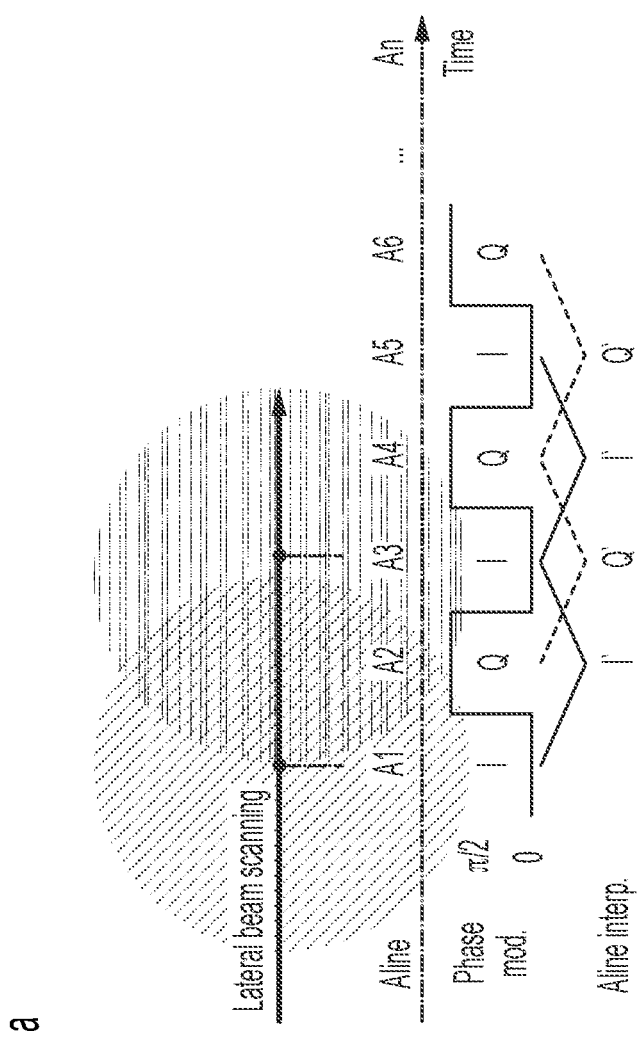
FIG. 19 shows A-line demodulation, including panels: (a) Schematic of A-line demodulation. (b),(c) Artefact suppression for mirror signals across the baseband showing the raw, dispersion compensated signals (b) and I,Q demodulated signals (c). FSR=100 GHz. The −1st, baseband and 1st order signals are indicated. (d) Measured complex conjugate suppression of a mirror signal over a time period of one hour.
Figure 19:
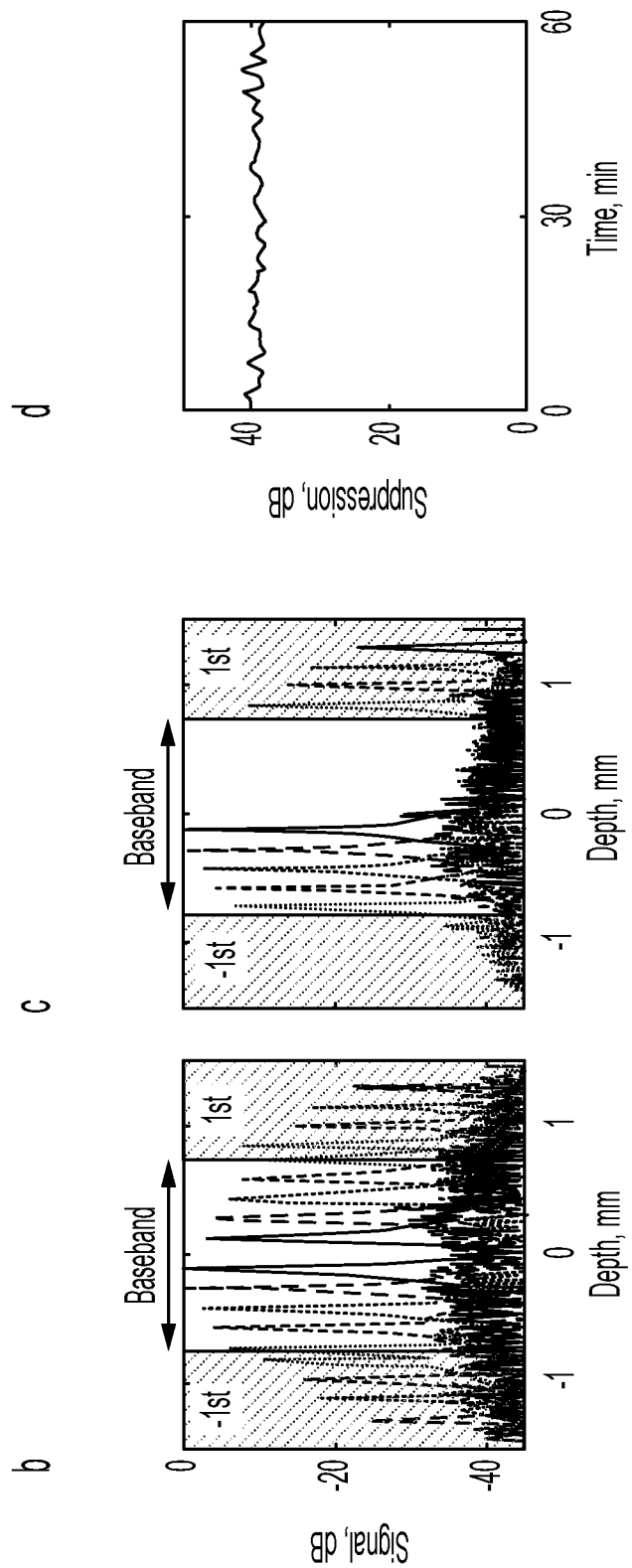

The concept of inter A-line demodulation is illustrated in FIG. 19 panel (a). In this method, a phase modulator in the reference arm induced phase shifts between alternating A-lines during lateral scanning. Odd and even A-lines represented the I and Q quadrature components, $A_{I,Q}$, respectively, which were used to form the analytic depth signal as $S(z)=S_I(z)+S_Q(z)=FFT\{A_I(\omega)\}+FFT\{\sqrt{-1}A_Q(\omega)\}$. A-line demodulation requires high phase stability between A-lines and high A-line rates to avoid phase noise from sample motion. The high phase stability due to dispersion based sweeping and the high repetition rate of SPML laser make them an excellent candidate for A-line demodulation. For an A-line separation much less than the beam spot size, A-lines are correlated and provide valid I,Q components. For large step sizes, the acquired A-lines correspond to different spatial locations and are increasingly uncorrelated, leading to reduced suppression. In that case, suppression can be retrieved by complex A-line interpolation.

A Galvo scanner (Thorlabs) was employed with a fast axis frequency of 504.3 Hz. The frequency was set to a multiple integer of the master clock (pattern generator external clock). The phase modulation frequency was adjusted to half the A-line rate, $f_{PM}$=3.7 MHz. This had to be carefully selected to match a multiple integer of the laser repetition rate for synchronization. The sampling rate was adjusted to $f_s$=3.87 GS/s, which conveniently matched the pattern generator clock rate, yielding 389 points per A-line and a Nyquist depth of 1.5 mm.

FIG. 19 panels (b) and (c) show A-lines with PSFs across the principal measurement range before (FIG. 19 panel (b)) and after (FIG. 19 panel (c)) I,Q demodulation using a FSR of 100 GHz ($L_B$=1.5 mm). The 100 GHz FSR only requires a sampling rate of $f_s$=1.94 GS/s. To also demonstrate first order artefact suppression, we deliberately oversampled the optical Nyquist frequency. Note that no lateral beam scanning was applied in this case and complex interpolation was applied. The suppression of complex conjugate terms in the baseband as well as the ±1st order is clear and approximately 40 dB. The suppression measurement was limited to the system noise floor. Coherent averaging (100 A-lines) revealed a suppression down to a −50 dB noise floor. The demodulation was highly stable and permanent, without any need for readjustment for days. For demonstration, the suppression was continuously measured for one hour without interfering (FIG. 19 panel (d)).

Complex Averaging

For lateral beam step sizes larger than the beam spot size, phase modulated A-lines are increasingly uncorrelated and yield reduced complex conjugate term suppression as I and Q A-lines correspond to different spatial locations. The lateral beam step size can be relaxed to a quarter of the beam spot size by complex interpolating (or complex averaging). The Q quadrature component is obtained at the spatial location of its I counterpart by interpolating neighboring Q A-line spatial locations (and vice versa) in the depth domain after Fourier transformation.

Figure 20:
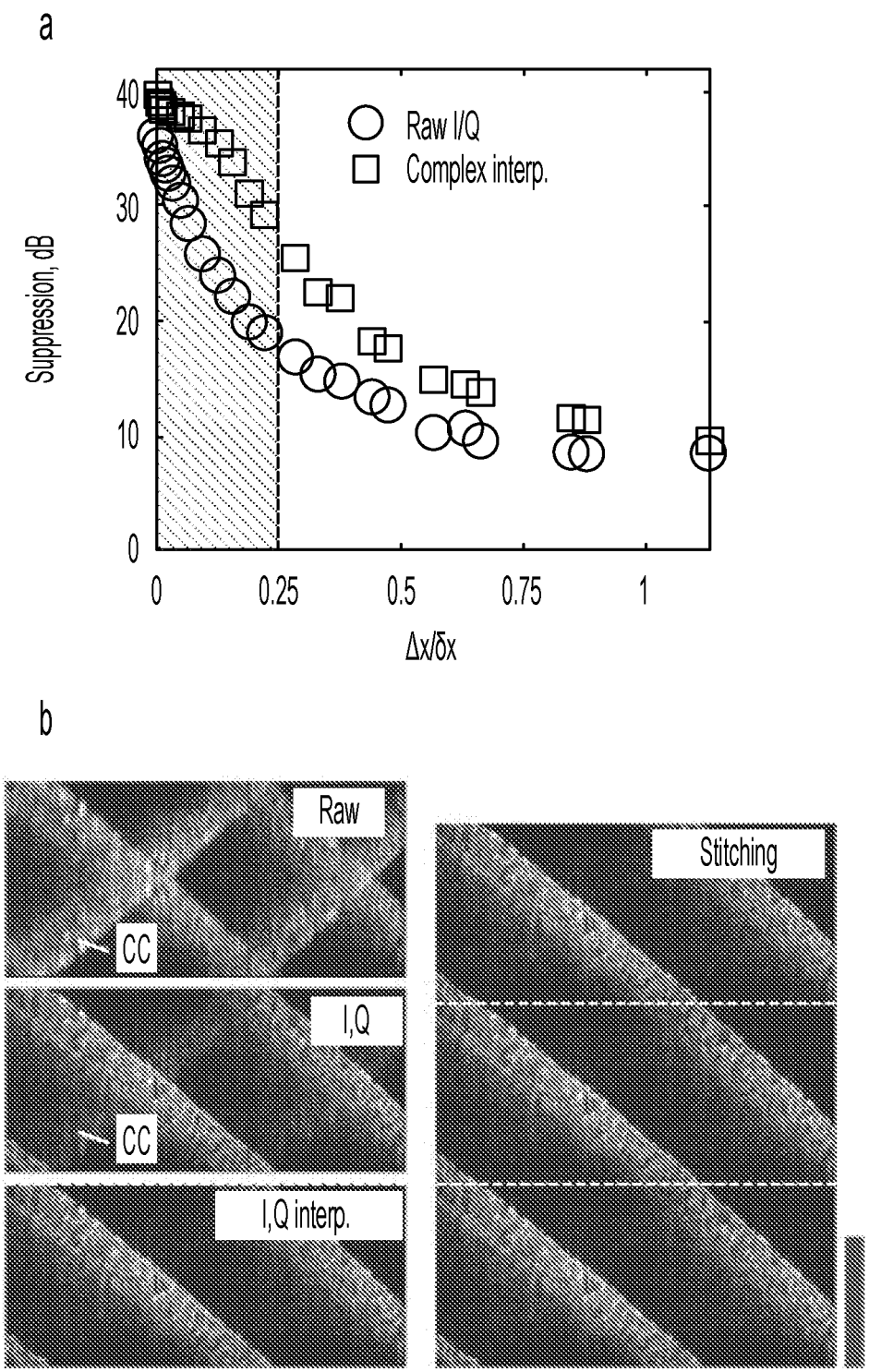
FIG. 20 shows complex interpolation, including panels: (a) Measured suppression before (circles) and after complex interpolation (squares) as a function of beam step size, $\Delta x$, normalized to the beam spot size, $\delta x$. (b) Imaging example of an IR card illustrating complex interpolation. It is shown the raw image and I,Q demodulated image. The demodulated image was stitched three times to make the borderless wrapping of sample structure beyond the baseband range clear. The FSR was 100 GHz ($L_B$=1.5 mm). Scale bar corresponds to 1 mm.

FIG. 20 panel (a) demonstrates the measured complex conjugate term suppression as a function of beam step size normalized to the beam diameter, $\Delta x/\delta x$, where $\delta x$ corresponds to twice the Gaussian beam waist parameter, $\delta x=4\lambda_0 F/(\pi D)$, with F being the lens focal length and D being the collimated beam diameter. In this work, the beam step size was adjusted by changing the scanning amplitude, while maintaining the scanning frequency. The green area indicates valid beam step sizes where neighboring A-lines are sufficiently correlated ($\Delta x \leq \frac{1}{4}\delta x$). Complex interpolation enhanced suppression by approximately 10 dB for step sizes smaller than a quarter of the beam spot size. It shows that spatial oversampling and complex interpolation can yield a suppression better than 35 dB. Note that the 40 dB suppression limit for small step sizes was due to the system noise floor and does not represent the hard limit of this technique. For beam step sizes smaller than $\Delta x/\delta x$=0.1, the suppression after interpolation plateaus around 40 dB, indicating a potential suppression better than 40 dB for systems that offer better noise performance. In summary, the application of this technique is limited by the beam step size, which either compromises lateral scanning speed (B-scan rate) or scanning amplitude (field of view). FIG. 20 panel (b) shows an example of complex interpolation by imaging an IR card using a beam step size of $\Delta x/\delta x$=0.23. The raw image clearly shows complex conjugate terms (labeled 'cc' in FIG. 20, panel (b)). I,Q demodulation offers suppression but artefacts remained visible. Complex interpolation further improves suppression, reducing the artefacts to the −30 dB noise floor that was typically observed during imaging. Finally, the demodulated and corrected image was stitched three times to make the borderless wrapping of sample structure that exceeded the baseband range clearer.

Imaging

Figure 21:
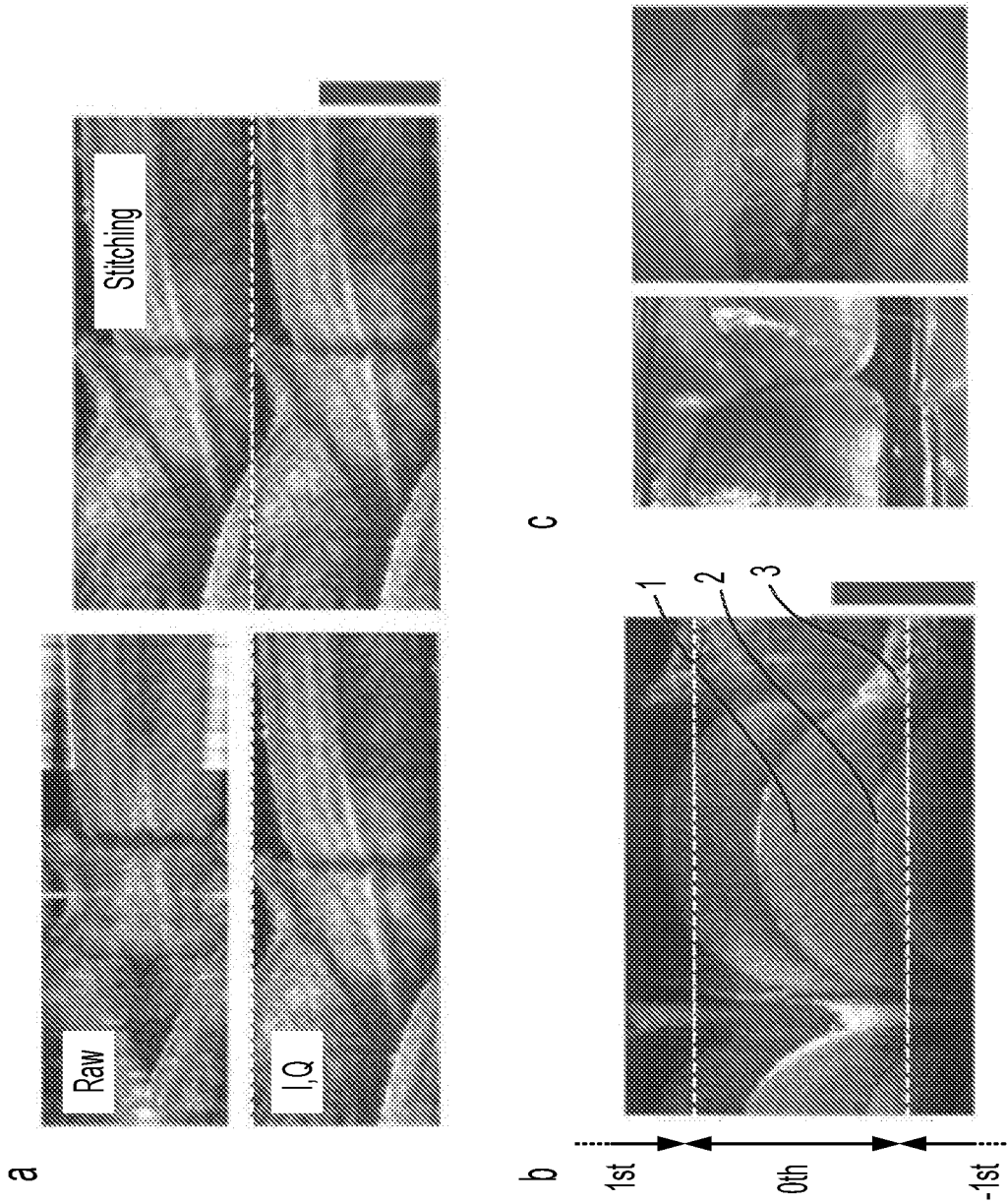
FIG. 21 shows imaging examples using A-line demodulation, including panels: (a) Cross-sectional images of a human nail fold showing the raw, dispersion compensated image (upper left) and the I,Q demodulated image (lower left). The demodulated image is stitched twice (right) to make the borderless wrapping of structure exceeding the frequency comb principal measurement range clear. (b) I,Q demodulated image of a human tooth showing the enamel (1), dentin (2) and gum (3). For illustrative purpose, we here show the entire acquisition range, where the baseband range is indicated by dashed, yellow lines. (c) Volumetric depth projections showing human teeth at 15 volumes per second using a 50 mm lens (left) and 150 mm lens (right). Scale bars correspond to 1 mm.

An imaging example of a human nail fold is demonstrated in FIG. 21 panel (a). Shown are the raw, dispersion compensated image as well as the artefact free I,Q demodulated image. The beam step size was $\Delta x/\delta x$=0.15. No complex interpolation was applied. A FSR of 100 GHz was used and the images only show the baseband range, i.e., $L_B$=1.5 mm. The I,Q demodulated image was stitched twice on top of itself in order to make the borderless wrapping of sample structure exceeding the baseband more clear. Moreover, FIG. 21 panels (b) and (c) show imaging of human teeth using a FSR of 100 GHz. Distinct layers showing the enamel (1), dentin (2) and gum (3) are visible in FIG. 21 panel (b). No complex interpolation was required. For illustrative purpose, here the entire acquisition depth range is exclusively plotted, as opposed to only the baseband range as seen in all previous images. The baseband is indicated by dashed, yellow lines. Sample structure exceeding the baseband (top yellow line) into the 1st order is folded back into the bottom of the baseband, whereas structure reaching into the −1st order (bottom yellow line) is wrapped back into the top of the baseband. The structure above the enamel surface is thus the bottom of the tooth that is folded into the top of the baseband. The high imaging depth of teeth suggests a larger baseband (smaller FSR) in order to avoid overlapping structure. Finally, SPML-based circular ranging is used to demonstrate volumetric, video camera-like imaging of teeth at 15 volumes per second, using a 50 mm lens (FIG. 21 panel (c), left) and 200 mm lens (FIG. 1 panel (c), right). As for the frame demodulation technique, this represents a 50-fold compression factor in digitizer bandwidth and data load for signal and image processing compared to a continuously swept laser with similar performance. Together with the imaging of layers shown in FIG. 21 panel (b), this illustrates the versatility of medical and industrial applications offered by the simultaneous high speed and long range of circular ranging.

Thus, a CFBG-based SPML laser at 1.3 µm has been demonstrated for the first time, making this design available for a more suitable wavelength region of OCT. The laser had an A-line rate of 7.6 MHz and a duty cycle of 76%. The sweep speed was 194 THz/µs, allowing a maximum of 10 MHz at full duty cycle. The sweep range was 100 nm and coherence length 4 cm, while the FSR, i.e., principal measurement range, was continuously adjustable. Circular ranging OCT was implemented by complex demodulation with inter A-line phase modulation using a $LiNbO_3$ phase modulator. Frame demodulation had no speed limitation and in principle is only limited by the B-scan rate. Demodulation was demonstrated at 2 kHz using two phase modulated frames from a 4 kHz resonant scanner. Small phase variations due to axial optical path changes in the microscope of the sample arm were corrected by applying a global phase correction. B-scan rates in the 6-10 kHz range are desirable to further minimize this phase noise.

A-line demodulation was demonstrated as a second inter A-line demodulation technique that constructed the complex analytic signal from two A-lines, phase modulated at 3.7 MHz (half the A-line rate). The application of this technique is restricted by use of a beam step size that requires spatial oversampling, which either compromises lateral scanning speed (B-scan rate) or scanning amplitude (field of view). For sufficient oversampling, neighboring A-lines are correlated and offer suppression up to 40 dB, which was only limited by the system noise floor. Larger step sizes sacrificed suppression. In this case, complex interpolation enhanced suppression by approximately 10 dB for step sizes smaller than a quarter of the beam spot size. The active demodulation methods presented herein are highly stable, require minimal or no post-processing, are wavelength independent, and may be performed using a single acquisition channel. Together with the CFBG-based SPML, this can provide embodiments of compact and stable circular ranging imaging systems.

Figure 22:
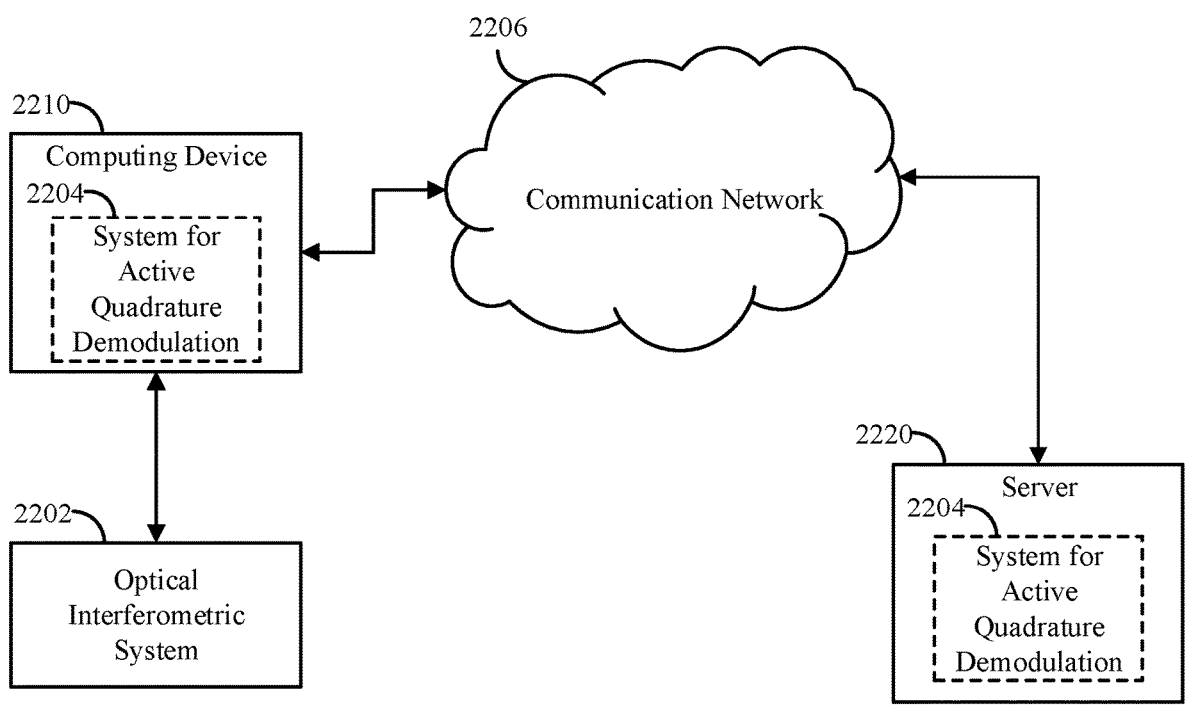
FIG. 22 shows an example of a system for active quadrature demodulation for circular ranging optical coherence tomography in accordance with some embodiments of the disclosed subject matter.

Turning to FIG. 22, an example 2200 of a system for active quadrature demodulation for circular ranging optical coherence tomography is shown in accordance with some embodiments of the disclosed subject matter. As shown in FIG. 22, a computing device 2210 can receive in-phase data and/or quadrature data from an optical interferometric system 2200. In some embodiments, computing device 2210 can execute at least a portion of a system for active quadrature demodulation 2204 to determine a complex interference signal based on the in-phase data and/or quadrature data received from optical interferometric system 2200. Additionally or alternatively, in some embodiments, computing device 2210 can communicate information about the in-phase data and/or quadrature data received from optical interferometric system 2200 to a server 2220 over a communication network 2206, which can execute at least a portion of system for active quadrature demodulation 2204 to determine a complex interference signal based on the in-phase data and/or quadrature data. In some such embodiments, server 2220 can return information to computing device 2210 (and/or any other suitable computing device) indicative of an output of system for active quadrature demodulation 2204, such as the complex interference signal. This information may be transmitted and/or presented to a user (e.g. a researcher, an operator, a clinician, etc.) and/or may be stored (e.g. as part of a research database or a medical record associated with a subject).

In some embodiments, computing device 2210 and/or server 2220 can be any suitable computing device or combination of devices, such as a desktop computer, a laptop computer, a smartphone, a tablet computer, a wearable computer, a server computer, a virtual machine being executed by a physical computing device, etc. As described herein, system for active quadrature demodulation 2204 can present information about the in-phase data, the quadrature data, and/or the complex interference signal to a user (e.g., researcher and/or physician).

In some embodiments, electro-magnetic radiation source 2202 can be any source suitable for optical interferometry such as CR-OCT. In some embodiments, electro-magnetic radiation source 2202 can be local to computing device 2210. For example, electro-magnetic radiation source 2202 may be incorporated with computing device 2210 (e.g., computing device 2210 can be configured as part of a device for capturing and/or storing optical interferometric information). As another example, electro-magnetic radiation source 2202 may be connected to computing device 2210 by a cable, a direct wireless link, etc. Additionally or alternatively, in some embodiments, electro-magnetic radiation source 2202 can be located locally and/or remotely from computing device 2210, and can communicate information to computing device 2210 (and/or server 2220) via a communication network (e.g., communication network 2206).

In some embodiments, communication network 2206 can be any suitable communication network or combination of communication networks. For example, communication network 2206 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. In some embodiments, communication network 2206 can be a local area network, a wide area network, a public network (e.g., the Internet), a private or semi-private network (e.g., a corporate or university intranet), any other suitable type of network, or any suitable combination of networks. Communications links shown in FIG. 22 can each be any suitable communications link or combination of communications links, such as wired links, fiber optic links, Wi-Fi links, Bluetooth links, cellular links, etc.

Figure 23:
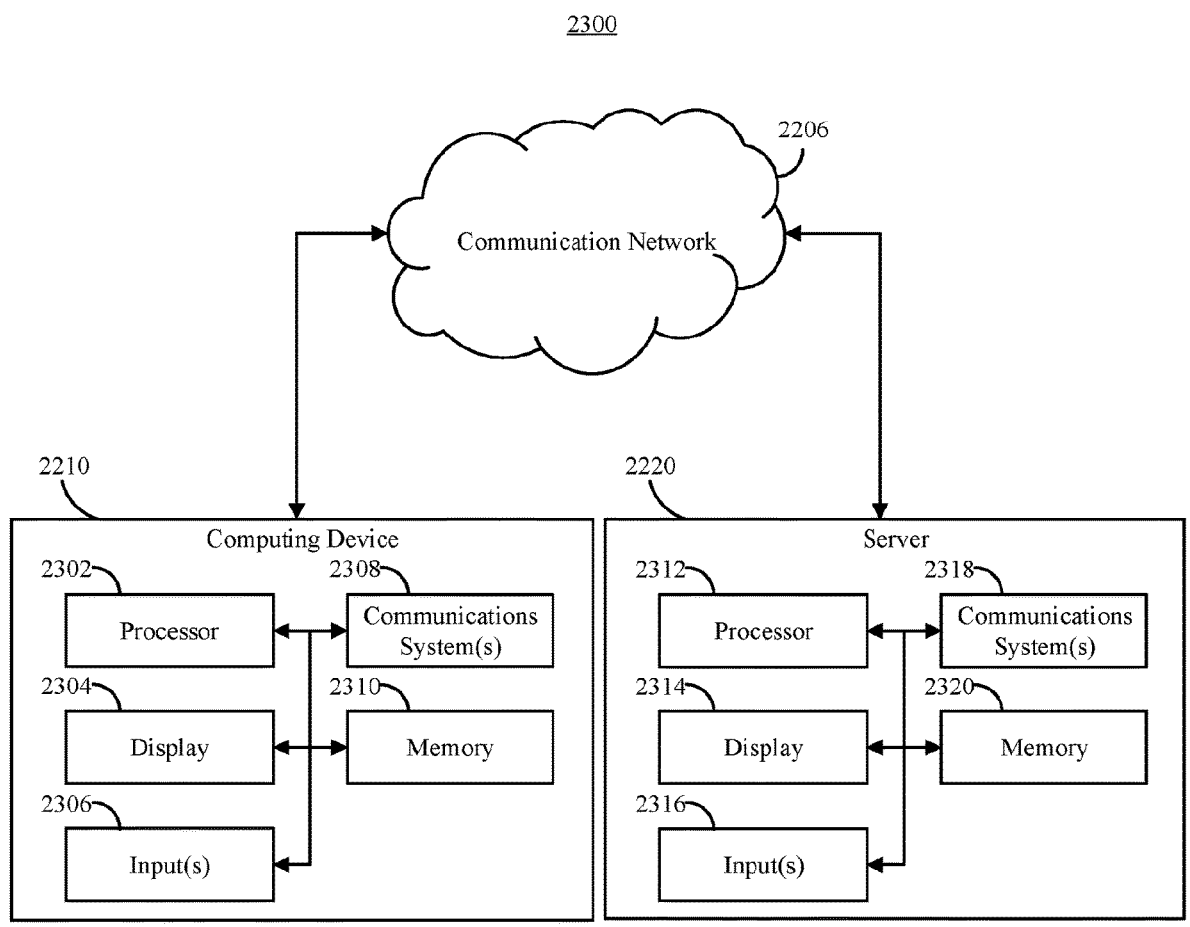
FIG. 23 shows an example of hardware that can be used to implement computing device and server in accordance with some embodiments of the disclosed subject matter.

FIG. 23 shows an example 2300 of hardware that can be used to implement computing device 2210 and server 2220 in accordance with some embodiments of the disclosed subject matter. As shown in FIG. 23, in some embodiments, computing device 2210 can include a processor 2302, a display 2304, one or more inputs 2306, one or more communication systems 2308, and/or memory 2310. In some embodiments, processor 2302 can be any suitable hardware processor or combination of processors, such as a central processing unit, a graphics processing unit, etc. In some embodiments, display 2304 can include any suitable display devices, such as a computer monitor, a touchscreen, a television, etc. In some embodiments, inputs 2306 can include any suitable input devices and/or sensors that can be used to receive user input, such as a keyboard, a mouse, a touchscreen, a microphone, etc.

In some embodiments, communications systems 2308 can include any suitable hardware, firmware, and/or software for communicating information over communication network 2206 and/or any other suitable communication networks. For example, communications systems 2308 can include one or more transceivers, one or more communication chips and/or chip sets, etc. In a more particular example, communications systems 2308 can include hardware, firmware and/or software that can be used to establish a Wi-Fi connection, a Bluetooth connection, a cellular connection, an Ethernet connection, etc.

In some embodiments, memory 2310 can include any suitable storage device or devices that can be used to store instructions, values, etc., that can be used, for example, by processor 2302 to present content using display 2304, to communicate with server 2220 via communications system(s) 2308, etc. Memory 2310 can include any suitable volatile memory, non-volatile memory, storage, or any suitable combination thereof. For example, memory 2310 can include RAM, ROM, EEPROM, one or more flash drives, one or more hard disks, one or more solid state drives, one or more optical drives, etc. In some embodiments, memory 2310 can have encoded thereon a computer program for controlling operation of computing device 2210. In such embodiments, processor 2302 can execute at least a portion of the computer program to present content (e.g., images, user interfaces, graphics, tables, etc.), receive content from server 2220, transmit information to server 2220, etc.

In some embodiments, server 2220 can include a processor 2312, a display 2314, one or more inputs 2316, one or more communications systems 2318, and/or memory 2320. In some embodiments, processor 2312 can be any suitable hardware processor or combination of processors, such as a central processing unit, a graphics processing unit, etc. In some embodiments, display 2314 can include any suitable display devices, such as a computer monitor, a touchscreen, a television, etc. In some embodiments, inputs 2316 can include any suitable input devices and/or sensors that can be used to receive user input, such as a keyboard, a mouse, a touchscreen, a microphone, etc.

In some embodiments, communications systems 2318 can include any suitable hardware, firmware, and/or software for communicating information over communication network 2206 and/or any other suitable communication networks. For example, communications systems 2318 can include one or more transceivers, one or more communication chips and/or chip sets, etc. In a more particular example, communications systems 2318 can include hardware, firmware and/or software that can be used to establish a Wi-Fi connection, a Bluetooth connection, a cellular connection, an Ethernet connection, etc.

In some embodiments, memory 2320 can include any suitable storage device or devices that can be used to store instructions, values, etc., that can be used, for example, by processor 2312 to present content using display 2314, to communicate with one or more computing devices 2210, etc. Memory 2320 can include any suitable volatile memory, non-volatile memory, storage, or any suitable combination thereof. For example, memory 2320 can include RAM, ROM, EEPROM, one or more flash drives, one or more hard disks, one or more solid state drives, one or more optical drives, etc. In some embodiments, memory 2320 can have encoded thereon a server program for controlling operation of server 2220. In such embodiments, processor 2312 can execute at least a portion of the server program to transmit information and/or content (e.g., results of a tissue identification and/or classification, a user interface, etc.) to one or more computing devices 2210, receive information and/or content from one or more computing devices 2210, receive instructions from one or more devices (e.g., a personal computer, a laptop computer, a tablet computer, a smartphone, etc.), etc.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

In some embodiments, the optical signals are detected by photodiodes. It should be recognized that any option-electronic conversion device including but not limited to photo detectors, photodiodes, line-scan and two-dimensional cameras, and photodiode arrays can be used to perform this detection function.

It should be noted that while the embodiments describe the induction of a 90 degree phase shift between measurements to generate complex signals, it is known that these complex signals can be generated from measurements that are phase shifted by values other than 90 degrees using for example correction routines in post-processing. Thus, the embodiments can be configured also go generate phase shifts that are non-zero, but not necessarily 90 degrees, to create complex signals.

It should be noted that, as used herein, the term mechanism can encompass hardware, software, firmware, or any suitable combination thereof.

Figure 24:
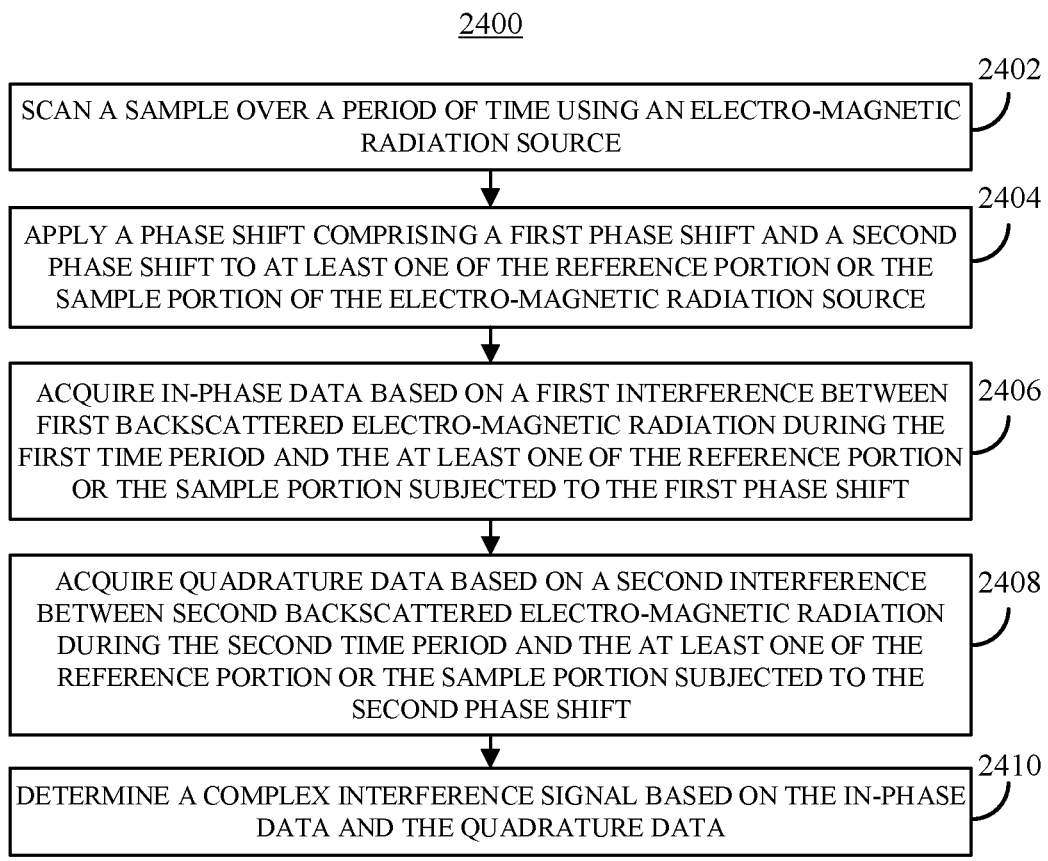
FIG. 24 shows an example of a process for active quadrature demodulation for circular ranging optical coherence tomography in accordance with some embodiments of the disclosed subject matter.

FIG. 24 shows an example 2400 of a process for active quadrature demodulation for circular ranging optical coherence tomography in accordance with some embodiments of the disclosed subject matter. As shown in FIG. 24, at 2402, process 2400 can scan a sample over a period of time using an electro-magnetic radiation source. The period of time may include a first time period and a second time period, a sample portion of the electro-magnetic radiation source may be directed to the sample in a sample arm of an optical interferometric system, and a reference portion of the electro-magnetic radiation source may be directed to a reference arm of the optical interferometric system. At 2404, process 2400 can apply a phase shift including a first phase shift and a second phase shift to at least one of the reference portion or the sample portion of the electro-magnetic radiation source. The phase shift may be applied using a phase modulator, the first phase shift may be applied during the first time period and the second phase shift may be applied during the second time period, and the second phase shift may have a difference of 90 degrees from the first phase shift. At 2406, process 2400 can acquire in-phase data based on a first interference between first backscattered electro-magnetic radiation during the first time period and the at least one of the reference portion or the sample portion subjected to the first phase shift. At 2408, process 2400 can acquire quadrature data based on a second interference between second backscattered electro-magnetic radiation during the second time period and the at least one of the reference portion or the sample portion subjected to the second phase shift. Finally, at 2410, process 2400 can determine a complex interference signal based on the in-phase data and the quadrature data.

Figure 25:
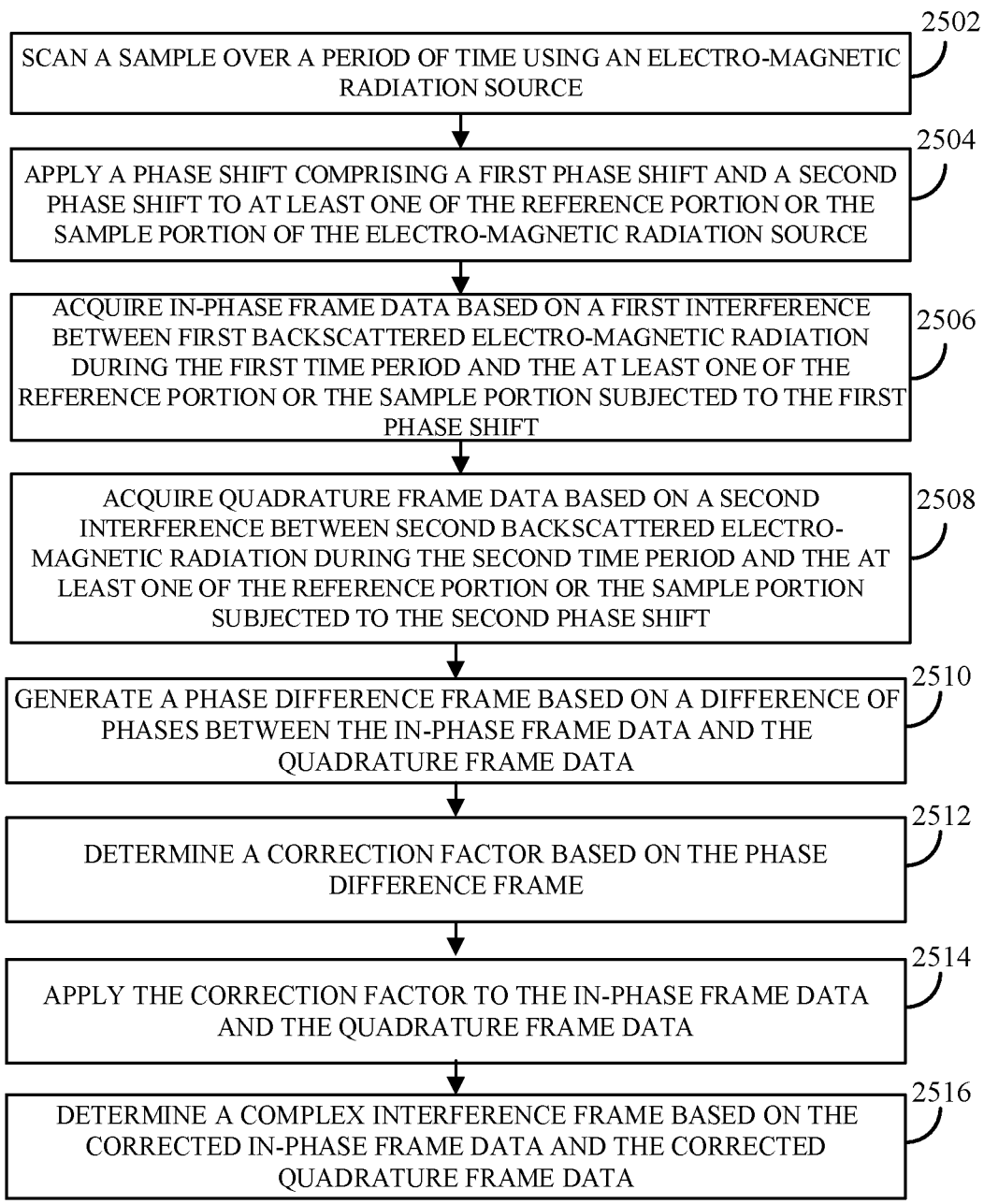
FIG. 25 shows an example of another process for active quadrature demodulation for circular ranging optical coherence tomography in accordance with some embodiments of the disclosed subject matter.

FIG. 25 shows an example 2500 of another process for active quadrature demodulation for circular ranging optical coherence tomography in accordance with some embodiments of the disclosed subject matter. As shown in FIG. 25, at 2502, process 2500 can scan a sample over a period of time using an electro-magnetic radiation source. The period of time may include a first time period and a second time period, a sample portion of the electro-magnetic radiation source may be directed to the sample in a sample arm of an optical interferometric system, and a reference portion of the electro-magnetic radiation source may be directed to a reference arm of the optical interferometric system. At 2504, process 2500 can apply a phase shift including a first phase shift and a second phase shift to at least one of the reference portion or the sample portion of the electro-magnetic radiation source. The phase shift may be applied using a phase modulator, the first phase shift may be applied during the first time period and the second phase shift may be applied during the second time period, and the second phase shift may have a difference of 90 degrees from the first phase shift. At 2506, process 2500 can acquire in-phase frame data based on a first interference between first backscattered electro-magnetic radiation during the first time period and the at least one of the reference portion or the sample portion subjected to the first phase shift. At 2508, process 2500 can acquire quadrature frame data based on a second interference between second backscattered electro-magnetic radiation during the second time period and the at least one of the reference portion or the sample portion subjected to the second phase shift. At 2510, process 2500 can generate a phase difference frame based on a difference of phases between the in-phase frame data and the quadrature frame data. At 2512, process 2500 can determine a correction factor based on the phase difference frame. At 2514, process 2500 can apply the correction factor to the in-phase frame data and the quadrature frame data. Finally, at 2516, process 2500 can determine a complex interference frame based on the corrected in-phase frame data and the corrected quadrature frame data.

It should be understood that the above described steps of the processes of FIGS. 24 and 25 can be executed or performed in any order or sequence not limited to the order and sequence shown and described in the figures. Also, some of the above steps of the processes of FIGS. 24 and 25 can be executed or performed substantially simultaneously where appropriate or in parallel to reduce latency and processing times.

Thus, while the invention has been described above in connection with particular embodiments and examples, the invention is not necessarily so limited, and that numerous other embodiments, examples, uses, modifications and departures from the embodiments, examples and uses are intended to be encompassed by the claims attached hereto.

What is claimed is:

1. A method, comprising:
    scanning a sample over a period of time using an electro-magnetic radiation source, the period of time including a first time period and a second time period, scanning the sample comprising:
        emitting from the electro-magnetic radiation source a plurality of electro-magnetic radiation pulses each divided into two time periods corresponding to the first time period and the second time period,
        directing a sample portion of the plurality of electro-magnetic radiation pulses from the electro-magnetic radiation source to the sample in a sample arm of an optical interferometric system, and
        directing a reference portion of the plurality of electro-magnetic radiation pulses from the electro-magnetic radiation source to a reference arm of the optical interferometric system;
    applying, using a phase modulator, a phase shift comprising a first phase shift and a second phase shift to at least one of the reference portion or the sample portion of the electro-magnetic radiation source,
        the first phase shift being applied during the first time period and the second phase shift being applied during the second time period,
        the second phase shift having a difference of 90 degrees from the first phase shift;
    acquiring in-phase data based on a first interference between first backscattered electro-magnetic radiation during the first time period and the at least one of the reference portion or the sample portion subjected to the first phase shift;
    acquiring quadrature data based on a second interference between second backscattered electro-magnetic radiation during the second time period and the at least one of the reference portion or the sample portion subjected to the second phase shift; and
    determining a complex interference signal based on the in-phase data and the quadrature data.

2. The method of claim 1, wherein the first phase shift is 0 degrees during the first time period and the second phase shift is 90 degrees during the second time period.

3. The method of claim 2,
    wherein applying a phase shift further comprises:
        applying the phase shift to the reference portion of the electro-magnetic radiation source,
    wherein acquiring in-phase data further comprises:
        acquiring the in-phase data based on the first interference between the first backscattered electro-magnetic radiation during the first time period and the reference portion subjected to the first phase shift,
    wherein acquiring quadrature data further comprises:
        acquiring the quadrature data based on the second interference between the second backscattered electro-magnetic radiation during the second time period and the reference portion subjected to the second phase shift, and
    wherein determining a complex interference signal further comprises:
        determining the complex interference signal based on the in-phase data and the quadrature data.

4. The method of claim 1,
    wherein the plurality of electro-magnetic radiation pulses includes a first A-line comprising a first subset of the plurality of electro-magnetic radiation pulses emitted during the first time period and a second A-line comprising a second subset of the plurality of electro-magnetic radiation pulses emitted during the second time period, and wherein scanning the sample further comprises:
    scanning the sample using the first A-line during the first time period and the second A-line during the second time period.

5. The method of claim 4, wherein the first subset of the plurality of electro-magnetic radiation pulses corresponds to a particular sequence of wavenumbers, and
    wherein the second subset of the plurality of electro-magnetic radiation pulses corresponds to the particular sequence of wavenumbers.

6. The method of claim 5, wherein a first wavenumber of the particular sequence of wavenumbers is different from a second wavenumber of the particular sequence of wavenumbers.

7. The method of claim 6, wherein the first A-line is scanned at a first location in the sample and the second A-line is scanned at a second location in the sample different from the first location.

8. The method of claim 7, wherein the electro-magnetic radiation source emits a third A-line comprising a third subset of the plurality of electro-magnetic radiation pulses emitted during a third time period and corresponding to the particular sequence of wavenumbers,
wherein scanning the sample further comprises:
scanning the sample using the third A-line during the third time period;
wherein applying the phase shift further comprises:
applying a 0 degree phase shift to the reference portion of the electro-magnetic radiation source during the third time period;
wherein the in-phase data comprises first in-phase data,
wherein the quadrature data comprises second quadrature data,
wherein acquiring in-phase data further comprises:
acquiring third in-phase data based on a third interference between third backscattered electro-magnetic radiation during the third time period and the 0-degree shifted reference portion; and
wherein determining the complex interference signal further comprises:
determining second in-phase data based on interpolating between the first in-phase data and the third in-phase data, and
determining the complex interference signal based on the second in-phase data and the second quadrature data.

9. The method of claim 8, wherein the electro-magnetic radiation source emits a beam having a beam diameter,
wherein a distance between the first location and the second location is one quarter of the beam diameter or less.

10. The method of claim 1, wherein the method further comprises:
providing a modified electro-magnetic radiation source configured to combine the plurality of electro-magnetic radiation pulses with a delayed copy of the plurality of electro-magnetic radiation pulses; and
wherein scanning the sample further comprises:
scanning the sample using the modified electro-magnetic radiation source,
wherein the modified electro-magnetic radiation source emits the plurality of electro-magnetic pulses each occurring during the first time period alternating with the respective plurality of delayed pulses each occurring during the second time period.

11. The method of claim 10, wherein providing the modified electro-magnetic radiation source further comprises:
providing the modified electro-magnetic radiation source configured to combine the plurality of electro-magnetic radiation pulses with the respective delayed copy of the plurality of electro-magnetic radiation pulses,
wherein the delayed copy of the plurality of electro-magnetic radiation pulses is delayed by a time less than a time of one of the plurality of the electro-magnetic radiation pulses.

12. The method of claim 11, wherein determining the complex interference signal further comprises:
determining the complex interference signal based on applying a depth dependent calibration to correct for additional phase shift from a detection system.

13. The method of claim 1, wherein acquiring in-phase data further comprises:
acquiring an in-phase frame associated with the first phase shift;
wherein acquiring quadrature data further comprises:
acquiring a quadrature frame associated with the second phase shift; and
wherein the method further comprises:
generating a phase difference frame based on a difference of phases between the in-phase frame and the quadrature frame,
determining a correction factor based on the phase difference frame,
applying the correction factor to the in-phase frame and the quadrature frame, and
determining a complex interference frame based on the corrected in-phase frame and the corrected quadrature frame.

14. The method of claim 13, wherein determining a correction factor further comprises:
determining a mean phase difference based on the phase difference frame, and
determining the correction factor based on a difference between the mean phase difference and a 90 degree phase shift.

15. The method of claim 14, wherein determining the mean phase difference further comprises:
determining a histogram of phase differences in the phase difference frame, and
identifying the mean phase difference based on the histogram of phase differences.

16. The method of claim 1, wherein the electro-magnetic radiation source comprises an optically subsampled wavelength stepped source (OSWSS).

17. The method of claim 1, wherein the electro-magnetic radiation source comprises a chirped fiber Bragg grating stretched-pulse mode-locked (CFBG-SPML) laser.

18. The method of claim 17, wherein the CFBG-SPML laser comprises a 1.3 µm imaging band.

19. The method of claim 1, wherein the phase modulator comprises a lithium niobate phase modulator.

20. An apparatus, comprising:
an optical interferometricsystem comprising a sample arm and a reference arm;
at least one phase modulator associated with at least one of the reference arm or the sample arm of the optical interferometricsystem;
an electro-magnetic radiation source coupled to the optical interferometric system,
the electro-magnetic radiation source-configured to:
emit a plurality of electro-magnetic radiation pulses each divided into two time periods corresponding to the first time period and the second time period,
the optical interferometricsystem configured to:
scan a sample over a period of time, the period of time including a first time period and a second time period,
direct a sample portion of the plurality of electro-magnetic radiation pulses from the electro-magnetic radiation source to the sample in the sample arm of the optical interferometricsystem, and direct a reference portion of the plurality of electro-magnetic radiation pulses from the electro-magnetic radiation source to the reference arm of the optical interferometricsystem, the at least one phase modulator being configured to:
apply a phase shift comprising a first phase shift and a second phase shift to at least one of the reference portion or the sample portion of the electro-magnetic radiation source,
apply the first phase shift during the first time period, and
apply the second phase shift-during the second time period, the second phase shift having a difference of 90 degrees from the first phase shift; and a microprocessor coupled to the phase modulator and the electro-magnetic radiation source, the microprocessor to:
acquire in-phase data based on a first interference between first backscattered electro-magnetic radiation during the first time period and the at least one of the reference portion or the sample portion subjected to the first phase shift,
acquire quadrature data based on a second interference between second backscattered electro-magnetic radiation during the second time period and the at least one of the reference portion or the sample portion subjected to the second phase shift, and
determine a complex interference signal based on the in-phase data and the quadrature data.

21. The apparatus of claim 20, wherein the first phase shift is 0 degrees during the first time period and the second phase shift is 90 degrees during the second time period.

22. The apparatus of claim 21,
wherein the phase shift is applied to the reference portion of the electro-magnetic radiation source by the at least one phase modulator,
wherein the microprocessor, when acquiring in-phase data, is further to:
acquire the in-phase data based on the first interference between the first backscattered electro-magnetic radiation during the first time period and the reference portion subjected to the first phase shift,
wherein the microprocessor, when acquiring quadrature data, is further to:
acquire the quadrature data based on the second interference between the second backscattered electro-magnetic radiation during the second time period and the reference portion subjected to the second phase shift, and
wherein the microprocessor, when determining a complex interference signal, is further to:
determine the complex interference signal based on the in-phase data and the quadrature data.

23. The apparatus of claim 20,
wherein the plurality of electro-magnetic radiation pulses includes a first A-line comprising a first subset of the plurality of electro-magnetic radiation pulses emitted during the first time period and a second A-line comprising a second subset of the plurality of electro-magnetic radiation pulses emitted during the second time period, and wherein the electro-magnetic radiation source is further to:
scan the sample using the first A-line during the first time period and the second A-line during the second time period.

24. The apparatus of claim 23, wherein the first subset of the plurality of electro-magnetic radiation pulses corresponds to a particular sequence of wavenumbers, and
wherein the second subset of the plurality of electro-magnetic radiation pulses corresponds to the particular sequence of wavenumbers.

25. The apparatus of claim 24, wherein a first wavenumber of the particular sequence of wavenumbers is different from a second wavenumber of the particular sequence of wavenumbers.

26. The apparatus of claim 25, wherein the first A-line is scanned at a first location in the sample and the second A-line is scanned at a second location in the sample different from the first location.

27. The apparatus of claim 26, wherein the electro-magnetic radiation source emits a third A-line comprising a third subset of the plurality of electro-magnetic radiation pulses emitted during a third time period and corresponding to the particular sequence of wavenumbers,
wherein the electro-magnetic radiation source is further to:
scan the sample using the third A-line during the third time period;
wherein the phase modulator is further to:
apply a 0 degree phase shift to the reference portion of the electro-magnetic radiation source during the third time period;
wherein the in-phase data comprises first in-phase data,
wherein the quadrature data comprises second quadrature data,
wherein the microprocessor, when acquiring in-phase data, is further to:
acquire third in-phase data based on a third interference between third backscattered electro-magnetic radiation during the third time period and the 0-degree shifted reference portion; and
wherein the microprocessor, when determining the complex interference signal, is further
determine second in-phase data based on interpolating between the first in-phase data and the third in-phase data, and
determine the complex interference signal based on the second in-phase data and the second quadrature data.

28. The apparatus of claim 27, wherein the electro-magnetic radiation source emits a beam having a beam diameter,
wherein a distance between the first location and the second location is one quarter of the beam diameter or less.

29. The apparatus of claim 20, wherein the microprocessor is further to:
provide a modified electro-magnetic radiation source by combining the plurality of electro-magnetic radiation pulses with a delayed copy of the plurality of electro-magnetic radiation pulses; and
wherein the electro-magnetic radiation source is further to:
scan the sample using the modified electro-magnetic radiation source,
wherein the modified electro-magnetic radiation source emits the plurality of electro-magnetic pulses each occurring during the first time alternating with the respective plurality of delayed pulses each occurring during the second time.

30. The apparatus of claim 29, wherein the microprocessor, when providing the modified electro-magnetic radiation source, is further to:

provide the modified electro-magnetic radiation source by combining the plurality of electro-magnetic radiation pulses with the delayed copy of the plurality of electro-magnetic radiation pulses,
wherein the delayed copy of the plurality of electro-magnetic radiation pulses is delayed by a time less than a time of one of the plurality of the electro-magnetic radiation pulses.

31. The apparatus of claim 30, wherein the microprocessor, when determining the complex interference signal, is further to:
determine the complex interference signal based on applying a depth dependent calibration to correct for additional phase shift from a detection system.

32. The apparatus of claim 20, wherein the microprocessor, when acquiring in-phase data, is further to:
acquire an in-phase frame associated with the first phase shift;
wherein the microprocessor, when acquiring quadrature data, is further to:
acquire a quadrature frame associated with the second phase shift; and
wherein the microprocessor is further to:
generate a phase difference frame based on a difference of phases between the in-phase frame and the quadrature frame,
determine a correction factor based on the phase difference frame,
apply the correction factor to the in-phase frame and the quadrature frame, and
determine a complex interference frame based on the corrected in-phase frame and the corrected quadrature frame.

33. The apparatus of claim 32, wherein the microprocessor, when determining a correction factor, is further to:
determine a mean phase difference based on the phase difference frame, and
determine the correction factor based on a difference between the mean phase difference and a 90 degree phase shift.

34. The apparatus of claim 33, wherein the microprocessor, when determining the mean phase difference, is further to:
determine a histogram of phase differences in the phase difference frame, and
identify the mean phase difference based on the histogram of phase differences.

35. The apparatus of claim 20, wherein the electro-magnetic radiation source comprises an optically sub-sampled wavelength stepped source (OSWSS).

36. The apparatus of claim 20, wherein the electro-magnetic radiation source comprises a chirped fiber Bragg grating stretched-pulse mode-locked (CFBG-SPML) laser.

37. The apparatus of claim 36, wherein the CFBG-SPML laser comprises a 1.3 µm imaging band.

38. The apparatus of claim 20, wherein the at least one phase modulator comprises a lithium niobate phase modulator.

* * * * *

UNITED STATES PATENT AND TRADEMARK OFFICE
CERTIFICATE OF CORRECTION

PATENT NO. : 11,852,474 B2
APPLICATION NO. : 17/264165
DATED : December 26, 2023
INVENTOR(S) : Benjamin J. Vakoc et al.

It is certified that error appears in the above-identified patent and that said Letters Patent is hereby corrected as shown below:

In the Specification

Column 12, Line 28, "is i" should be --ts_i--.

Column 16, Line 20, "7C" should be --$\pi$--.

Column 16, Line 58, "7C" should be --$\pi$--.

Column 22, Line 47, "co" should be --$\omega$--.

In the Claims

Claim 20, Column 34, Line 49, "interferometricsystem" should be --interferometric system--.

Claim 20, Column 34, Line 53, "interferometricsystem" should be --interferometric system--.

Claim 20, Column 34, Line 60, "interferometricsystem" should be --interferometric system--.

Claim 20, Column 34, Line 67, "interferometricsystem" should be --interferometric system--.

Claim 20, Column 35, Line 4, "interferometricsystem" should be --interferometric system--.

Signed and Sealed this
Twelfth Day of March, 2024

Katherine Kelly Vidal
*Director of the United States Patent and Trademark Office*